United States Patent
Zhang et al.

(10) Patent No.: US 9,115,340 B2
(45) Date of Patent: Aug. 25, 2015

(54) MICROFLUIDIC CONTINUOUS FLOW DEVICE

(75) Inventors: Chi Zhang, Singapore (SG); Danny van Noort, Singapore (SG); Henry Yu, Singapore (SG)

(73) Assignee: AGENCY FOR SCIENCE TECHNOLOGY & RESEARCH, Connexis (SG)

( * ) Notice: Subject to any disclaimer, the term of this patent is extended or adjusted under 35 U.S.C. 154(b) by 812 days.

(21) Appl. No.: 13/058,079

(22) PCT Filed: Aug. 8, 2008

(86) PCT No.: PCT/SG2008/000293
§ 371 (c)(1), (2), (4) Date: Jun. 7, 2011

(87) PCT Pub. No.: WO2010/016800
PCT Pub. Date: Feb. 11, 2010

(65) Prior Publication Data
US 2011/0256574 A1 Oct. 20, 2011

(51) Int. Cl.
*C12M 3/00* (2006.01)
*C12N 1/04* (2006.01)
(Continued)

(52) U.S. Cl.
CPC ............. *C12N 1/04* (2013.01); *B01L 3/502761* (2013.01); *C12M 23/16* (2013.01);
(Continued)

(58) Field of Classification Search
None
See application file for complete search history.

(56) References Cited

U.S. PATENT DOCUMENTS 6,368,871 B1 4/2002 Christel et al.
7,390,463 B2 * 6/2008 He et al. .................. 422/504
(Continued)

FOREIGN PATENT DOCUMENTS

WO  WO 96/23879 A1  8/1996
WO  WO 01/04144 A2  1/2001
(Continued)

OTHER PUBLICATIONS

Prokop, Ales; Prokop, Zdenka; Schaffer, David; Kozlov, Eugene; Wikswo, John; Cliffel, David; Baudenbacher, Franz "Nanoliter Bioreactor: Long-Term Mammalian Cell Culture at Nanofabricated Scale" Biomedical Microdevices, Dec. 2004, 6(4), pp. 325-339 (DOI: 10.1023/B:BMMD.0000048564.37800.d6).*

(Continued)

*Primary Examiner* — Rosanne Kosson
*Assistant Examiner* — Aaron J Kosar
(74) *Attorney, Agent, or Firm* — Stout, Uxa & Buyan, LLP; Carlos A. Fisher

(57) ABSTRACT

A microfluidic continuous flow device comprising a channel which comprises a first and a second area wherein the first area of the channel is a compartment which is defined by partitioning elements and the second area of the channel is a space outside the compartment; wherein through passages which are formed between the partitioning elements are dimensioned such as to retain a biological material and optionally a sustained release composition which can be comprised in the compartment within the compartment; wherein the channel has a first inlet to the compartment through which biological material can be introduced into the compartment; a second inlet for introducing a cultivation medium into a space of the channel arranged outside of the compartment, and an outlet. The present invention further refers to methods of using the devices of the present invention and kits comprising the microfluidic continuous flow devices of the present invention.

24 Claims, 12 Drawing Sheets

Figure 1:

(51) Int. Cl.
 B01L 3/00 (2006.01)
 C12M 3/06 (2006.01)
 C12M 1/00 (2006.01)
 C12M 1/12 (2006.01)
 C12N 5/077 (2010.01)
 C12N 5/071 (2010.01)

(52) U.S. Cl.
 CPC .............. *C12M 23/34* (2013.01); *C12M 25/00* (2013.01); *C12M 29/10* (2013.01); *C12N 5/067* (2013.01); *C12N 5/0653* (2013.01); *C12N 5/0686* (2013.01); *C12N 5/0688* (2013.01); *B01L 2200/0668* (2013.01); *B01L 2300/0877* (2013.01); *B01L 2400/0487* (2013.01); *B01L 2400/086* (2013.01)

(56) References Cited

U.S. PATENT DOCUMENTS

| | | | |
|---|---|---|---|
| 2003/0049862 A1* | 3/2003 | He et al. | 436/180 |
| 2003/0215941 A1 | 11/2003 | Campbell et al. | |
| 2006/0019361 A1 | 1/2006 | Ng et al. | |
| 2006/0160243 A1 | 7/2006 | Tang et al. | |
| 2007/0037277 A1 | 2/2007 | Shuler et al. | |
| 2007/0077547 A1* | 4/2007 | Shvets et al. | 435/4 |
| 2007/0272000 A1 | 11/2007 | Kahl et al. | |
| 2008/0124779 A1* | 5/2008 | Oh et al. | 435/173.9 |
| 2008/0233607 A1* | 9/2008 | Yu et al. | 435/29 |
| 2010/0216241 A1* | 8/2010 | Yu et al. | 435/395 |

FOREIGN PATENT DOCUMENTS

| | | | |
|---|---|---|---|
| WO | WO 03/029462 A1 | | 4/2003 |
| WO | 2005100537 A1 | | 10/2005 |
| WO | 2006052223 A1 | | 5/2006 |
| WO | WO 2006052223 A1 * | | 5/2006 |
| WO | WO 20071008609 A2 | | 1/2007 |

OTHER PUBLICATIONS

Foley, Jo; Mashadi-Hossein, A; Fu, E; Finlayson, BA; Yager, P "Experimental and model investigation of the time-dependent 2-dimensional distribution of binding in a herringbone microchannel" Lab Chip, Feb. 21, 2008, 8, pp. 557-564 (DOI: 10.1039/B713644G).*
Andersson et al "Micromachined flow-through filter-chamber for chemical reactions on beads" Sensors and Actuators B, 2000, 67, 203-208.*
Lutolf et al., Nat. Biotechnol., Jan. 2005, vol. 23, No. 1, pp. 47-55.
Bhadriraju et al., Drug Discovery Today, Jun. 11, 2002, vol. 7, No. 11, pp. 612-620.
Kleinman et al., Semin. Cancer Biol., 2005, vol. 15, No. 5, pp. 378-386.
Badylak, S.F., Transplant Immunol., 2004, vol. 12, No. 3, pp. 367-377.
Grant et al., Cell, Sep. 8, 1989, vol. 58, No. 5, pp. 933-943.
Lam et al., Biomaterials, 2006, vol. 27, pp. 4340-4347.
Dertinger et al., Anal. Chem., 2001, vol. 73, pp. 1240-1246.
Toh et al., Lab on a Chip, 2007, vol. 7, pp. 302-309.
Abbott, A., Nature, Aug. 2003, vol. 424, No. 6951, pp. 870-872.
Greenberg et al., PNAS, Feb. 1984, vol. 81, No. 3, pp. 969-973.
Medof et al., Faseb J., Apr. 1996, vol. 10, No. 5, pp. 574-586.
Kellam et al., Chem. Soc. Rev., 2003, vol. 32, No. 6, pp. 327-337.
De Bank et al., Biotechnology Bioeng., 2007, vol. 97, No. 6, pp. 1617-1625.
Ong et al., Biomaterials, 2007, vol. 28, No. 25, pp. 3656-3667.
Zhao et al., Biomaterials, 2008, vol. 29, No. 27, pp. 3693-3702.
Chia et al., Tissue Engineering, 2000, vol. 6, No. 5, pp. 481-495.
Wen et al., Biomaterials, May 1991, vol. 12, pp. 374-384.
Wen et al., Biomaterials, 1995, vol. 16, pp. 325-335.
Wallace et al., Advanced Drug Delivery Reviews, 2003, vol. 55, pp. 1631-1649.
Iliades et al., FEBS Lett., 1997, vol. 409, pp. 437-441.
Stone et al., Journal of Immunological Methods, 2007, vol. 318, pp. 88-94.
Holt et al., Trends Biotechnol., Nov. 2003, vol. 21, No. 11, pp. 484-490.
Beste et al., Proc. Natl. Sci., USA, Mar. 1999, vol. 96., pp. 1898-1903.
Napolitano et al., Chemistry & Biology, 1996, vol. 3, No. 5, pp. 359-367.
Mosavi et al., Protein Science, 2004, vol. 13, No. 6, pp. 1435-1448.
Skerra, J., Mol. Recognit., 2000, vol. 13, pp. 167-187.
Silverman et al., Nature Biotechnology, Dec. 2005, vol. 23, No. 12, pp. 1556-1561.
Gill et al., Current Opinion in Biotechnology, 2006, vol. 17, pp. 653-658.
Kwon et al., J. Am. Chem. Soc., 2007, vol. 129, pp. 1508-1509.
Carothers et al., J. Am. Chem. Soc., 2004, vol. 126(16), pp. 5130-5137.
Hoppe-Seyler et al., J. Mol. Med., 2000, vol. 78(8), pp. 426-430.
Young et al., J. of Controlled Release, 2005, vol. 109, pp. 256-274.
Sheweita, S.A., Current Drug Metabolism, 2000, vol. 1, pp. 107-132.
Schaffler et al., Endocrine Reviews, 2006, vol. 27, No. 5., pp. 449-467.
Unger et al., Science, 2000, vol. 288, pp. 113-116.
Hiller et al., Anal. Biochem., 1995, vol. 227, pp. 251-254.
Toh et al., Analyst, 2008, vol. 133, No. 3, pp. 326-330.
Kushibiki et al., Curr. Drug Delivery, 2004, vol. 1, pp. 153-163.
Morimoto et al., J. Pharm. & Pharmacology, 2005, vol. 57, pp. 839-844.
PCT International Search Report dated Nov. 5, 2008 in related PCT Application No. PCT/SG2008/000293, 2 pages.
Supplemental European Search Report dated Aug. 2, 2012 in related European Application No. EP08794198, 6 pages.
Langer et al., "Tissue Engineering", May 14, 1993, Science, vol., 260, No. 5110, pp. 920-926.
Nerem et al., "The Study of the Influence of Flow on Vascular Endothelial Biology", 1998, Am. J. Med. Sci., vol. 316, No. 3, pp. 167-175.
Hans G. Schleger, 1992, Allgemeine Mikrobiologie, 7th Edition, p. 93.
Bunka et al., "Aptamers come of age—at last", Aug. 2006, Nat. Rev. Microbiol., vol. 4(8), pp. 588-596.
Gilbert, Scott F., "Cell-cell Communication in Development", Chapter 6, Developmental Biology, 6th Edition, Sinauer Associates, Inc., Publisher, 2000, pp. 149-153.
European Office Action, application No. 08794198.5, dated Oct. 6, 2014, 5 pages.

* cited by examiner

— 50μm

——— 20μm

MICROFLUIDIC CONTINUOUS FLOW DEVICE

FIELD OF THE INVENTION

A microfluidic continuous flow device comprising a channel which comprises a first and a second area wherein the first area of the channel is a compartment which is defined by partitioning elements and the second area of the channel is a space outside the compartment; wherein through passages which are formed between the partitioning elements are dimensioned such as to retain a biological material and optionally a sustained release composition which can be comprised in the compartment within the compartment; wherein the channel has a first inlet to the compartment through which biological material can be introduced into the compartment; a second inlet for introducing a cultivation medium into a space of the channel arranged outside of the compartment, and an outlet. The present invention further refers to methods of using the devices of the present invention and kits comprising the microfluidic continuous flow devices of the present invention.

BACKGROUND TO THE INVENTION

Cells exist within a complex microenvironment consisting of soluble factors (e.g. growth factors, cytokines, and chemokines), an insoluble extracellular matrix which contains proteins for cell adhesion and cell-matrix interactions, and neighboring cells that allow for extensive cell-cell interactions (Lutolf, M. P., Hubbell, J. A., et al., 2005, Nat. Biotechnol., vol. 23, no. 1, p. 47). In cell culture, the microenvironment experienced by the cells can reflect the physiological relevance to in vivo environment and affect cellular behavior (Bhadriraju, K., Chen, C. S., 2002, Drug Discovery Today, vol. 7, no. 11, p. 612). Currently, plenty of powerful tools have been developed at our convenience to create controllable microenvironments that mimic in vivo situations for experimental and therapeutic applications. Progenitor and stem cells for regeneration of desired tissue act in synergy with the soluble factors present in the extracellular microenvironment to navigate multiple differentiation pathways and produce corresponding cell types (Langer, R., Vacanti, J. P., 1993, Science, vol. 260, no. 5110, p. 920). Thus, the microenvironment experienced by stem cells, or known as stem cell niche, is considered to be meaningful in tissue engineering.

Bhadriraju, K. and Chen, C. S. (2002, Drug Discovery Today, vol. 7, no. 11, p. 612) has demonstrated that engineering in vivo-like cultures by creating cellular microenvironments can improve cell-based drug testing.

In order to create more in vivo-like microenvironments for cell culture, both natural and synthetic biomaterials have been chosen for fabricating platforms. Natural ECM, such as Matrigel™ (Kleinman, H. K., Martin, G. R., 2005, Semin. Cancer Biol., vol. 15, no. 5, p. 378) and small intestinal submucosa (SIS) (Badylak, S. F., 2004, Transplat Immunol., vol. 12, no. 3, p. 367), which contain a variety of encapsulated growth factors, have been isolated. They can serve as valuable tools to study the interplay between microenvironments and consequent cellular responses. It has been discovered that vascular endothelial cells cultured in Matrigel™ are able to form capillaries with a central lumen (Grant, D. S., Tashiro, K., 1989, Cell, vol. 58, no. 5, p. 933). However, natural systems complicate the process of identifying the role of individual factors in tissue formation.

Therefore, a need exists to provide further systems which allow creation of in vivo like cell micro environments.

SUMMARY OF THE INVENTION

In a first aspect the present invention refers to a microfluidic continuous flow device comprising:
  a channel comprising a first and a second area wherein the first area is a compartment which is defined by partitioning elements and the second area is a space outside the compartment;
    wherein through passages which are formed between the partitioning elements are dimensioned such as to retain a biological material and a sustained release composition which are comprised in the compartment within the compartment;
    wherein the sustained release composition is adapted to release at least one substance which supports cultivation of the biological material;
    wherein the channel has a first inlet to the compartment for introducing biological material into the compartment; a second inlet for introducing a cultivation medium into the space of the channel arranged outside of the compartment, and an outlet;
    wherein the second inlet and the outlet are arranged such as to allow a flow of cultivation medium through the channel.

In another aspect the present invention refers to a microfluidic continuous flow device comprising:
  a first channel and a second channel each comprising a first and a second area wherein the first area is a compartment which is defined by partitioning elements and the second area is a space outside the compartment;
    wherein each of the channels has a first inlet to the compartment, a second inlet for introducing a cultivation medium into the space of the channel arranged outside of the compartment, and an outlet;
    wherein each of the second inlets and each of the outlets are arranged such as to allow a flow of cultivation medium through the channel; and
    wherein each of the second inlet of the first and second channel is in fluid communication with a common cultivation medium feeding line.

In another aspect the present invention refers to a microfluidic continuous flow device comprising:
  a first channel and a second channel each comprising a first and a second area wherein the first area is a compartment which is defined by partitioning elements and the second area is a space outside the compartment;
    wherein each of the channels has a first inlet to the compartment, a second inlet for introducing a cultivation medium into the space of the channel arranged outside of the compartment, and an outlet;
    wherein each of the second inlets and each of the outlets are arranged such as to allow a flow of cultivation medium through the channel; and
    wherein the first and the second channel are fluidly connected to each other wherein the outlet of the first channel is fluidly connected with the second inlet of the second channel.

In still another aspect the present invention refers to a method of cultivating biological material in a microfluidic continuous flow device, wherein the method comprises:
  providing the microfluidic continuous flow device having a channel;
    wherein the channel comprises a first and a second area wherein the first area is a compartment which is defined by partitioning elements and the second area is a space outside the compartment;
  wherein through passages which are formed between the partitioning elements are dimensioned such as to retain a biological material and a sustained release composition inside the compartment;
  wherein the channel has a first inlet for introducing biological material into the compartment, a second inlet for introducing cultivation medium into the space of the channel arranged outside of the compartment, and an outlet;
  wherein the second inlet and the outlet are arranged such as to allow a flow of cultivation medium through the channel;
introducing a biological material and a sustained release composition into the compartment via the first inlet;
  wherein the sustained release composition releases at least one substance which supports cultivation of the biological material and which is not initially comprised in the cultivation medium; and transporting a cultivation medium for cultivation of the biological material through the channel via the second inlet.

In another aspect, the present invention refers to a method of cultivating biological material in a microfluidic continuous flow device, wherein the method comprises:

providing the microfluidic continuous flow device having a first and a second channel;

wherein each channel comprises a first and a second area wherein the first area is a compartment which is defined by partitioning elements and the second area is a space outside the compartment;

wherein through passages which are formed between the partitioning elements are dimensioned such as to retain a biological material inside the compartment;

wherein each channel has a first inlet for introducing biological material into the compartment, a second inlet for introducing cultivation medium into the space of the channel arranged outside of the compartment, and an outlet;

wherein each of the second inlets and each of the outlets are arranged such as to allow a flow of cultivation medium through the channel wherein each of the second inlets of the first and second channel is in fluid communication with a common cultivation medium feeding line;

introducing biological material into each of the compartments via each of the respective first inlets; and transporting a cultivation medium via the common cultivation medium feeding line through each of the two channels.

In another aspect the present invention refers to a method of cultivating biological material in a microfluidic continuous flow device, wherein the method comprises:

providing the microfluidic continuous flow device having a first and a second channel;

wherein each channel comprises a first and a second area wherein the first area is a compartment which is defined by partitioning elements and the second area is a space outside the compartment;

wherein through passages which are formed between the partitioning elements are dimensioned such as to retain a biological material inside the compartment;

wherein each channel has a first inlet for introducing biological material into the compartment, a second inlet for introducing cultivation medium into the space of the channel arranged outside of the compartment, and an outlet;

wherein each of the second inlets and each of the outlets are arranged such as to allow a flow of cultivation medium through the channel;

wherein the first and the second channel are fluidly connected to each other wherein the outlet of the first channel is fluidly connected with the second inlet of the second channel;

introducing biological material into each of the compartments via each of the respective first inlets; and transporting a cultivation medium through the first and second channel by introducing a cultivation medium into the first channel via the second inlet of the first channel.

In still another aspect the present invention refers to a kit comprising a microfluidic continuous flow device of the present invention and a biological material. In some examples the kit further comprises a sustained release composition which is comprised in the compartment.

In still another aspect the present invention refers to the use of a microfluidic continuous flow device of the present invention or to the use of a method of the present invention for carrying out cell migration studies or gene expression analysis, or cellular function and differentiation studies, or disease diagnosis, or drug metabolism or toxicity testing.

BRIEF DESCRIPTION OF THE DRAWINGS

The invention will be better understood with reference to the detailed description when considered in conjunction with the non-limiting examples and the accompanying drawings, in which:

FIG. 1 shows an assembled microfluidic continuous flow device with two channels. The left hand picture shows three independent streams present in the device. The two tubes comprising dark colored streams on the right side of the device next to the single tube comprising the grey colored stream supply the biological material into the compartment via the first inlet while the tube comprising the grey stream on the right side indicates the cultivation medium which is fed via a common cultivation medium feeding line into the two channels. On the left side of the left hand picture the tubes are shown which comprise the cultivation medium streams leaving the channel via the outlets. The right picture in FIG. 1 shows a close-up view of one of the channels. The dark colored stream indicates the biological material introduced into the compartment of the channel while the grey colored streams on the right and on the left side of the compartment show the flow of the cultivation medium through the channel in the space arranged or located outside the compartment. As can be further seen in this picture, the inlets and outlets of the device all penetrate a cover layer arranged on top of the channel in order to access the compartment and the space outside the compartment, respectively. A device as shown in FIG. 1 can comprise more than the two channels shown wherein those channels can be either connected to a common medium feeding line as presently shown in FIG. 1 or can be connected in series as described further below.

FIG. 2 shows gelatin microspheres which are located in the compartment of the channel of the microfluidic continuous flow device. FIG. 2A shows the distribution of gelatin microspheres during seeding of biological material into the compartment. The arrows denote some of the larger gelatin microspheres. FIGS. 2B and C show packing of a gelatin microspheres/cell mixture in the compartment of a channel of a microfluidic continuous flow device. FIG. 2B is a confocal image while FIG. 2C is the corresponding transmission image. FIGS. 2B and 2C show the distribution of microspheres in the cell mixture after seeding into the compartment. The microspheres are stained green (encircled areas) in FIG. 2B.

Figure 3:
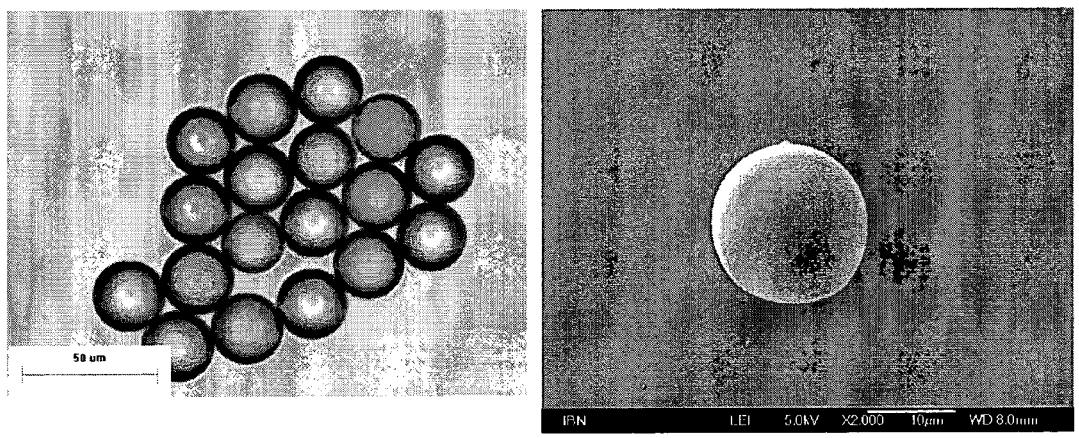

FIG. 3 shows a picture of gelatin microspheres fabricated by a water-in-oil emulsion technique. The microspheres shown have a diameter of about 25 μm (left hand picture) and about 17 μm (right hand picture).

Figure 4:
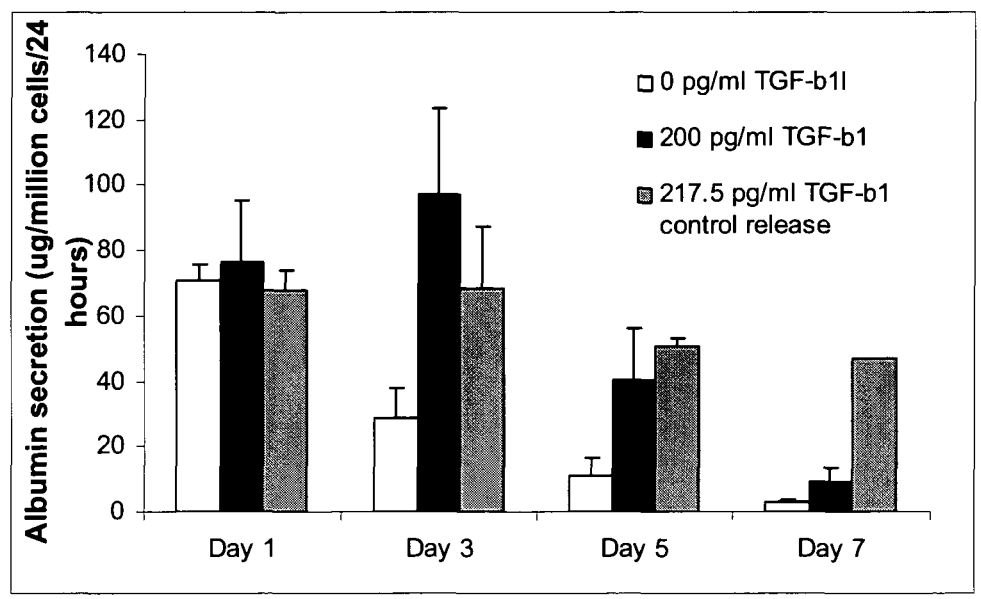

FIG. 4 shows the results of the evaluation of albumin secretion from primary rat hepatocytes cultured in a channel of a microfluidic continuous flow device. 200 pg/ml of TGF-β1 was supplemented into cultivation medium (■). In another set of experiment, TGF-β1 was pre-loaded into gelatin microspheres and was then controlled released to the hepatocytes at a concentration of 217.5 pg/ml (■). In the control experiment, there is no TGF-β1 supplemented in cultivation medium (□). In the presence of TGF-β1, the level of albumin secretion is enhanced. From day 5 onwards, when TGF-β1 is controlled released to the hepatocytes, the level of albumin secretion can be well-sustained while the albumin secretion decreases in the other two groups.

Figure 5:
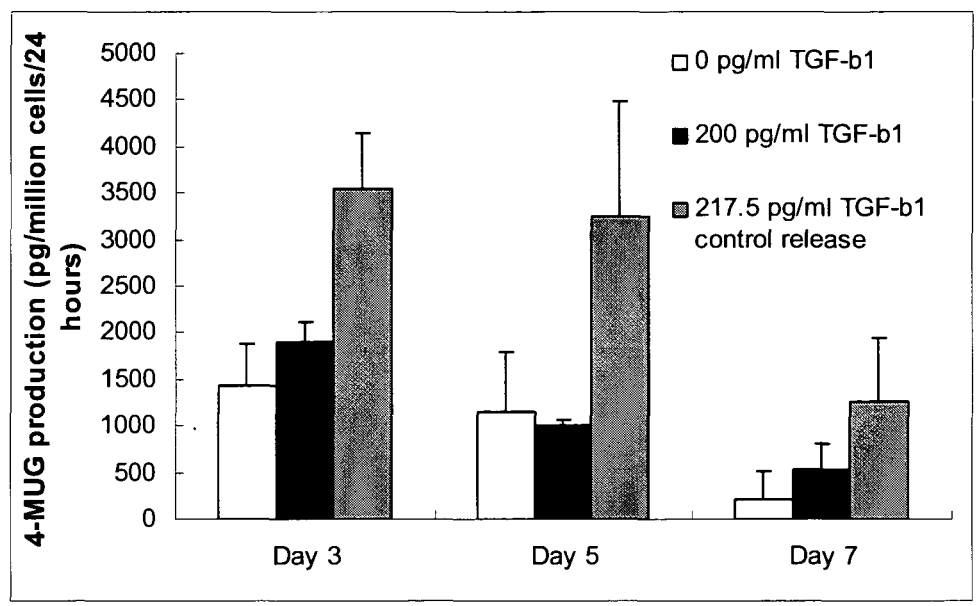

FIG. 5 shows the results of the evaluation of 4-MUG production of primary rat hepatocytes cultured in a channel of a microfluidic continuous flow device. 200 pg/ml of TGF-β1 was supplemented into cultivation medium (■). In another set of experiment, TGF-β1 was pre-loaded into gelatin microspheres and was then controlled released to the hepatocytes at a concentration of 217.5 pg/ml (■). In the control experiment, there is no TGF-β1 supplemented in cultivation medium (□). From day 3 onwards, when TGF-β1 is controlled released to the hepatocytes, the level of 4-MUG production is greatly enhanced compared to the other two groups.

Figure 6:
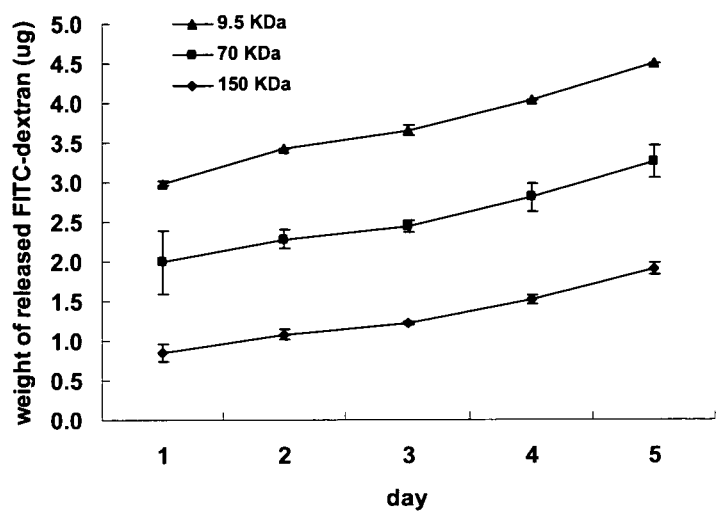

FIG. 6 shows the control release property of gelatin microspheres with a cross-linking density of 5%. The microspheres are loaded with FITC-dextran of 9.5 kDa, 70 kDa and 150 kDa which are used as probes to evaluate the release from the microspheres. On a daily basis, the amount of released molecule remains constant, which is indicative of the control release behavior of the gelatin microspheres.

Figure 7:
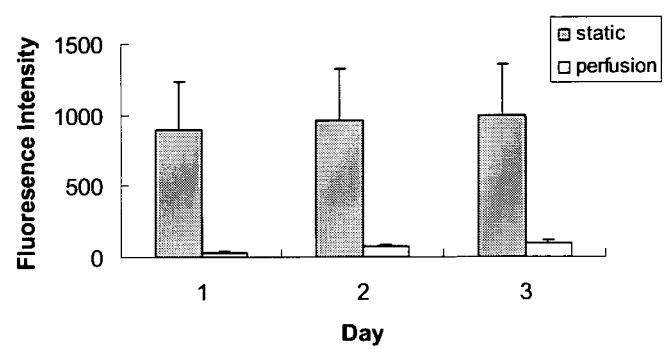

FIG. 7 shows a comparison of the amount of released molecules between static and flow through conditions. It was shown that since the accumulative amount of released FITC-dextran in perfusion (continuous flow through) was less than that in static, it can be concluded that released FITC-dextran remains in the compartment of the microfluidic channel. This proves that a soluble microenvironment can be created.

Figure 8:
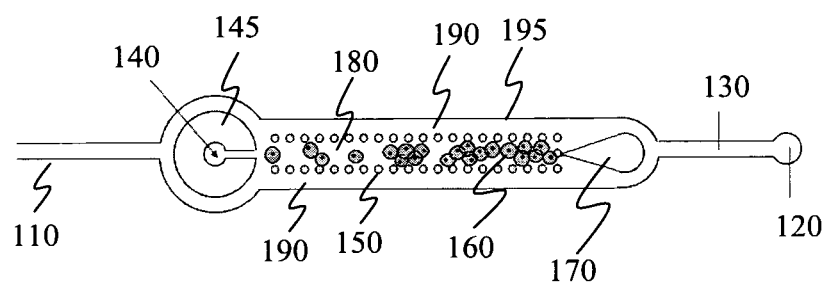

FIG. 8 shows an example of a channel of a microfluidic continuous flow device. The second inlet 110 feeding line feeds the channel 195 with cultivation medium which enters the channel through the second inlet and exits the channel through the outlet 120. 130 shows an additional exit channel fluidly connecting the outlet with the channel. Also shown is the first inlet 140 through which the biological material 160 is introduced into the compartment 180 of the channel 195. The compartment 180 is defined by partitioning elements 150. Also shown are the medium flow separator 145 and 170.

Figure 9:
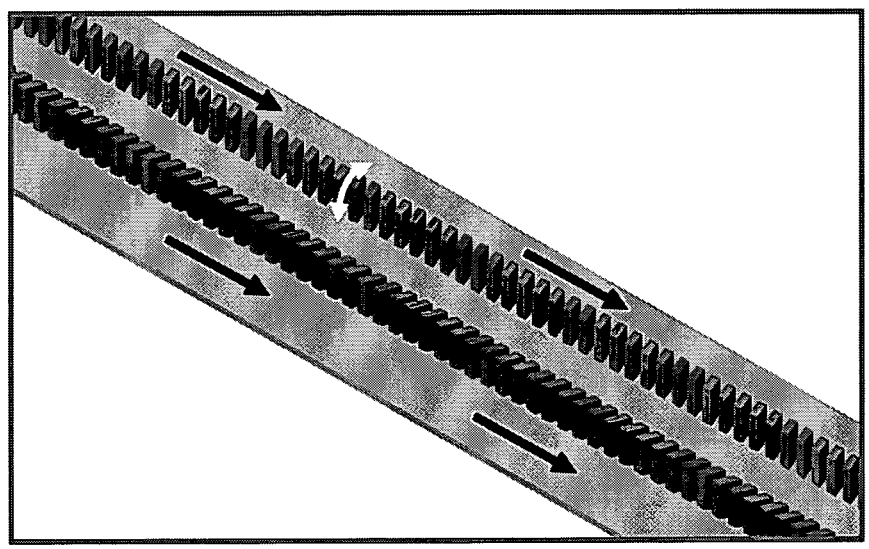

FIG. 9 illustrates the flow of the cultivation medium (black arrows) within the channel of a microfluidic continuous flow device. The compartment defined by the pillars is connected to the space outside the compartment by the through passages formed between the partitioning elements. Molecules can pass those through passages by liquid flow or diffusion (indicated by white bend arrow) depending on the width of the through passages or in other words on the distance between the partitioning elements.

Figure 10A:
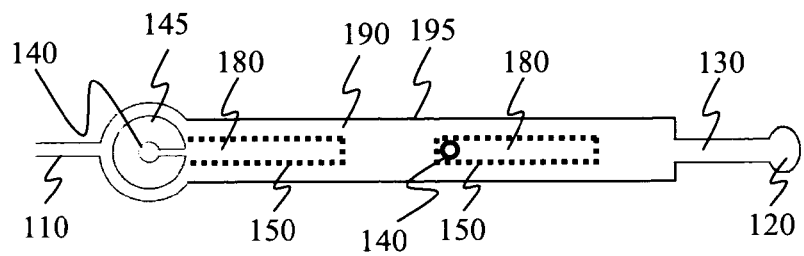
Figure 10B:
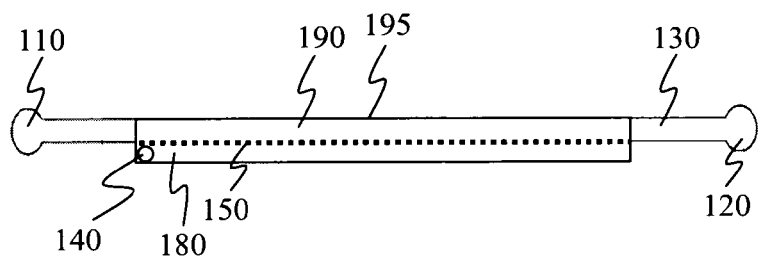

FIGS. 10 A and B show different examples of possible configurations of a microfluidic continuous flow device. In both FIGS. 10A and 10B, the cultivation medium enters the channel 195 through the second inlet channel 110 and exits it via the exit channel 130 and the outlet 120. The first inlet for the biological material 140 is comprised two times in the configuration shown in FIG. 10A and once in the configuration shown in FIG. 10B. In FIG. 10A the channel comprises two compartments 180 which can hold the same or different biological materials. The partitioning elements 150 define the compartment(s) 180. In FIG. 10B the channel comprises only one compartment which is defined at three sides by the circumferential wall of the channel and at one side by the partitioning elements 150.

Figure 11:
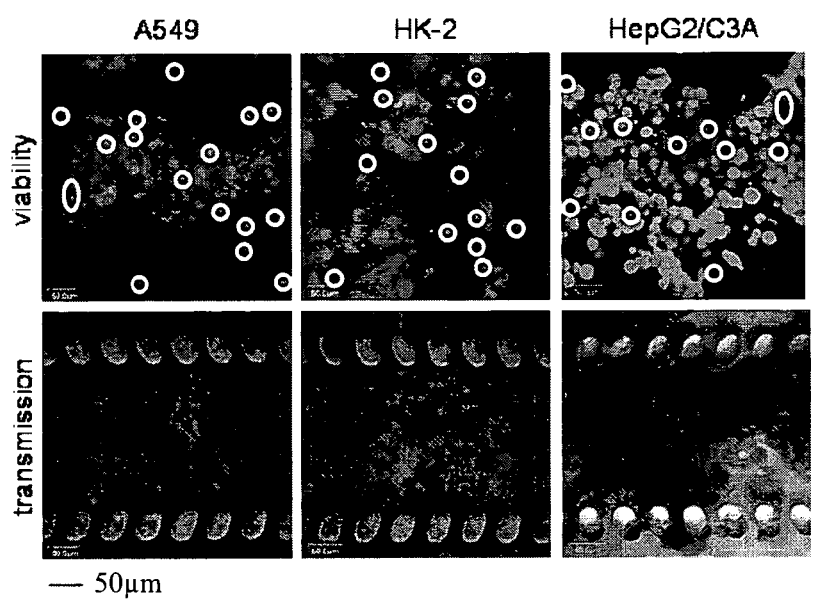

FIG. 11 shows the live/dead staining of cells cultured in the compartment of the microfluidic continuous flow device after 3 days. The encircled areas indicate dead cells while all other cells are alive. The upper panel of FIG. 11 shows the confocal images and the lower panel of FIG. 11 shows the corresponding transmission images.

Figure 12:
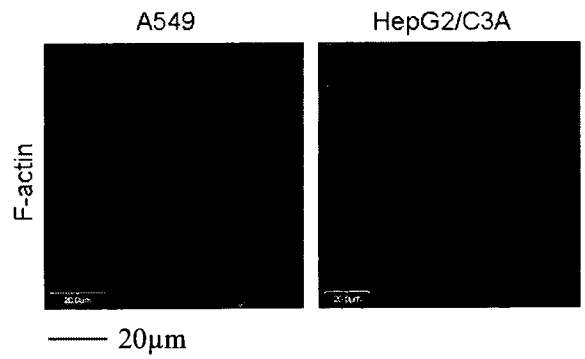

FIG. 12 shows the F-actin distribution of the cells cultured in the compartment of a channel of a microfluidic continuous flow device. The left picture shows the morphology of A549 cells and the right picture shows the morphology of HepG2/C3A cells. As can be seen in FIG. 12 the morphology of these A549 and HepG2/C3A cells resembles the natural (in vivo) three dimensional morphology of the cells when compared to two dimensional monolayers which can be observed for example when culturing those cells in a in culture flask.

Figure 13:
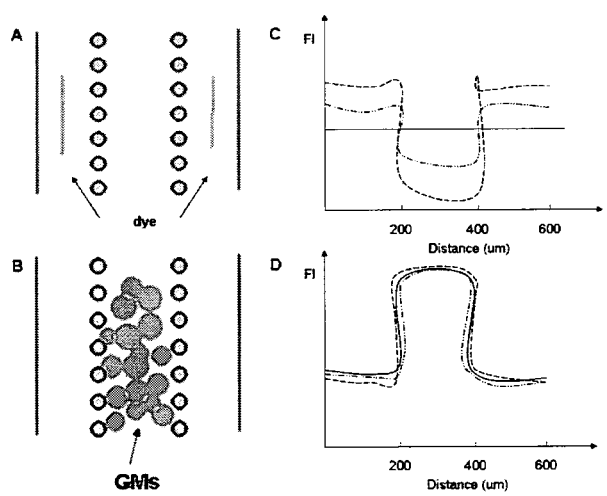
Figure 14:
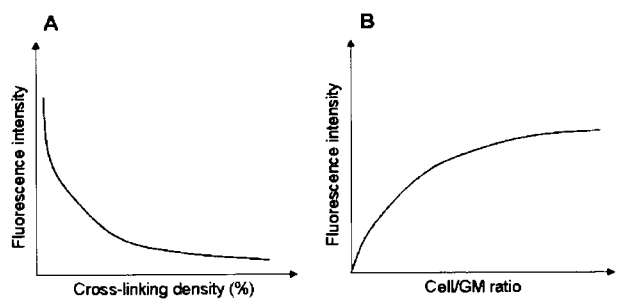

FIG. 13 shows the profile of the microenvironment in the microfluidic continuous flow device. FITC-dextran was used as probe to visualize the microenvironment. FIGS. 13A and 13B illustrate schematically the microfluidic channel filled with fluorescent dye and fluorescent gelatin microspheres, respectively. FIGS. 13C and 13D illustrate the fluorescence intensity (FI) measured over time in the channel. In FIGS. 13C and 13D the middle portion from 200 μm to 400 μm in the channel stands for the compartment while the part between 0 μm to 200 μm and 400 μm to 600 μm symbolizes the space outside the compartment. The dashed line is plotted after 10 minutes, dashed/dotted line is after one hour, and the solid line is after 2 hours. FIGS. 13A and 13C are the control. The y-axis in FIGS. 13C and 13D refers to the fluorescence intensity which was scanned over the entire width of the channel (0 to 600 μm; x-axis). The relation of the fluorescence intensity obtained is illustrated in FIG. 14 which shows that the fluorescence intensity decreases with the cross-linking density of the gelatin microspheres used while the fluorescence intensity increases with increasing cell/gelatin microsphere ratio.

Figure 15:
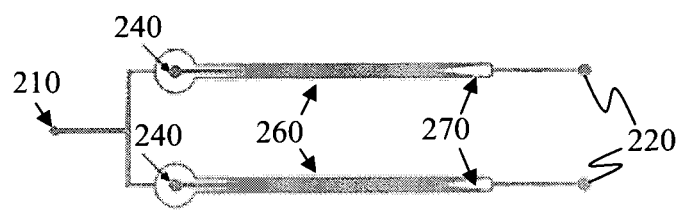

FIG. 15 is a schematic overview of the microfluidic continuous flow device shown in FIG. 1. 210 is the common second inlet channel through which the cultivation medium is fed into the channels 260. 240 show the first inlet for the biological material, 220 show the outlet while 270 show the medium flow separator located between the end of the compartments and the outlet channel.

Figure 16:
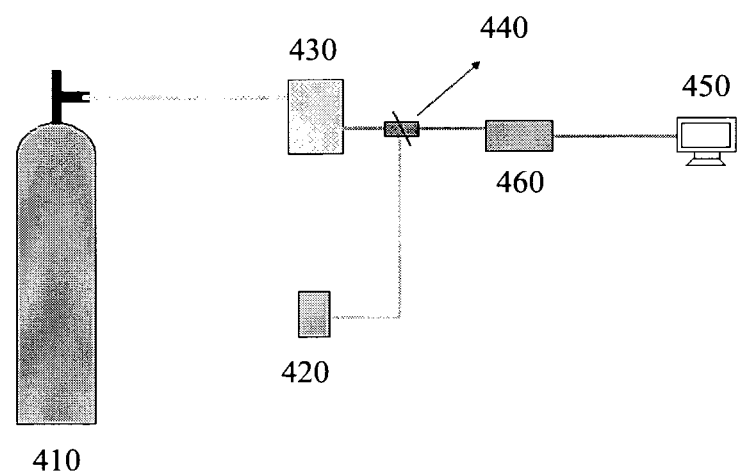
Figure 22:
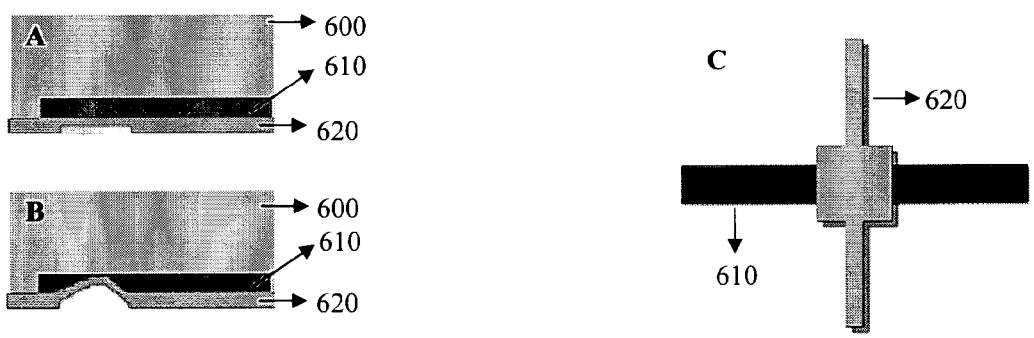

FIG. 16 illustrates the set-up of an exemplary operational control system. The gas tank 410 is connected by plastic tubings to a pressure regulator 430 which has a digital meter. By adjusting the meter, the pressure of gas is controlled that goes through the pressure regulator 430. The pressure regulator 430 is then connected to solenoid valves 440 that work as electrical switches. If they are switched on, gas can go through the solenoid valves 440 and cause deformation of the pneumatic valves in the microfluidic device 420. The solenoid valves are controlled by computer 450 through a 24 volt electric output 460. The pneumatic valves 420 are used to control the flow through the channels of the microfluidic continuous flow device by blocking and opening the passage through the channel as illustrated in FIG. 22.

Figure 17:
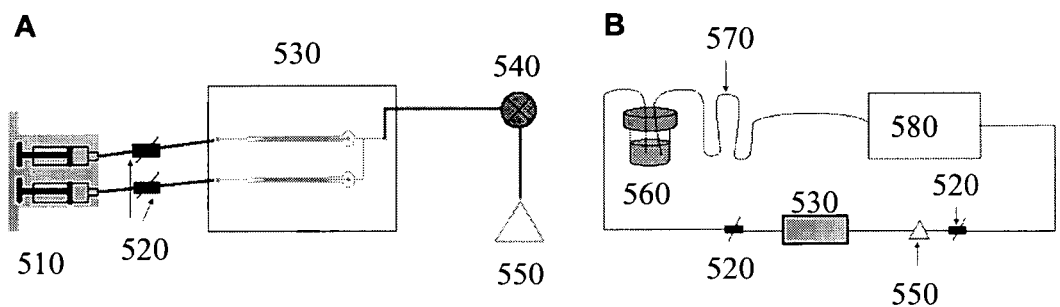

FIGS. 17 A and B illustrate the schematic set up of a continuous flow system including the microfluidic flow device. At first, cells are withdrawn from a cell reservoir (not shown in FIG. 17A) into the channels of the microfluidic flow device 530 by two withdrawal pumps 510 which are fluidly connected to the outlet (FIG. 17A). In FIG. 17B the cultivation medium is withdrawn from a cultivation medium storage tank 560 via a peristaltic pump 580. Oxygen permeable tubings 570 ensure that the oxygen level in the cultivation medium is sufficient for survival of the cells in the channel of the microfluidic flow device. After passing a regulative four way valve 520 and a bubble trap 550 the cultivation medium flows through the channel of the microfluidic device 530. As can be seen from FIG. 17B, cultivation medium from the two channels is sufficiently mixed in the cultivation medium storage tank 560 before being infused into the channels again.

Figure 18:
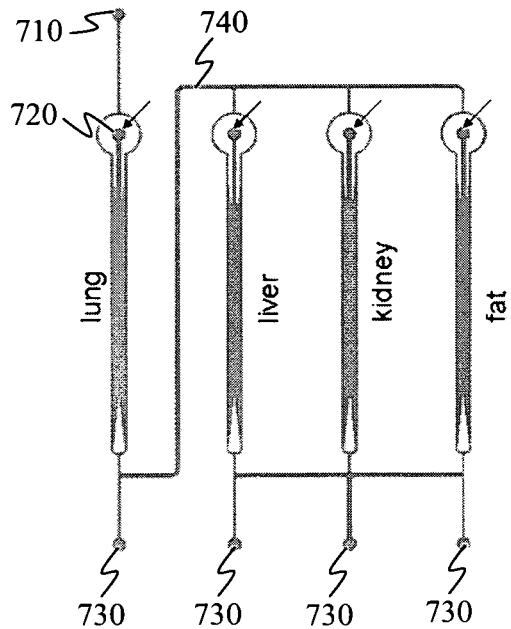

FIG. 18 shows a microfluidic flow device of the present invention which has one second inlet 720 and four outlets 730 which are fluidly connected to external valves. During perfusion culture, the outlet at the lung channel 730 is closed, so that cultivation medium will perfuse the lung cells comprised in the compartment of the first channel (designated "lung") first and flow via the feeding line 740 in parallel into the rest three channels. This flow profile is the same as physiological circulatory that blood comes from the lung and get distributed in the other organs. Each channel has an individual first inlet which is fluidly connected to a cell reservoir (indicated by black arrows) which is meant for cell seeding into the compartment of the respective channels.

Figure 19:
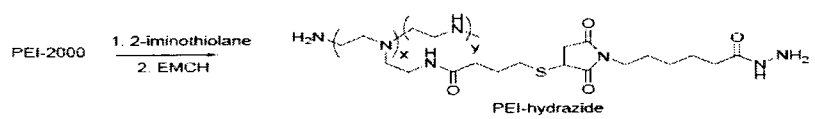
Figure 19:
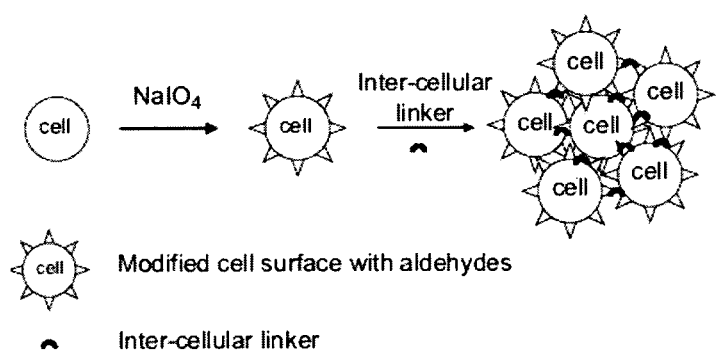

FIG. 19 shows in a diagram the synthesis route of the transient intercellular linkers, PEI-hy. The lower part of FIG. 19 shows a schematic representation of a cell aggregation process using intercellular linkers. For example, cell surfaces modified by sodium periodate ($NaIO_4$) display aldehyde groups which react with the hydrazides on the inter-cellular linker to form multi-cellular aggregates.

Figure 20:
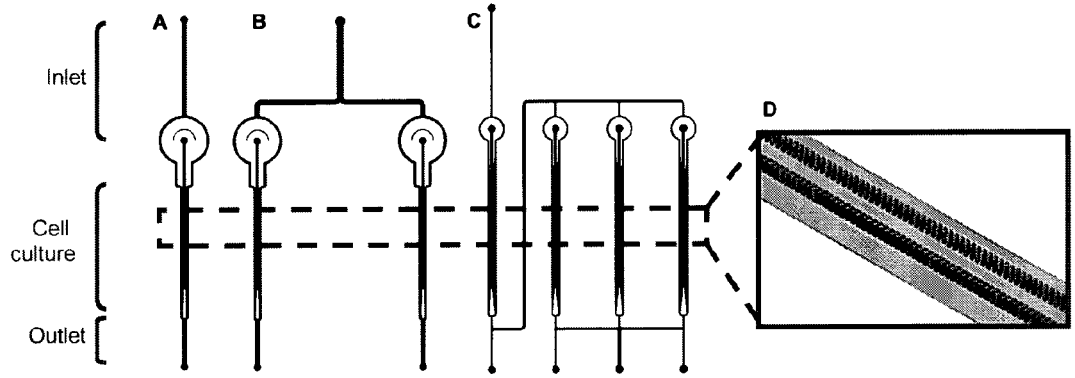

FIG. 20 shows a schematic representation of three different configurations of a microfluidic continuous flow device. FIG. 20A shows a single-channel system which comprises a biological material and a sustained release composition in the compartment of the channel. FIG. 20B shows a two-channel system with a common cultivation medium feeding line fluidly connected to each channel and FIG. 20C shows a four-channel system in which the outlet of the first channel is connected via a feeding line with the second inlet of three subsequent channels. FIG. 20D is an enlarged close up showing the partitioning elements defining the compartment comprised in the microfluidic continuous flow device which serves to entrap biological material such as cells.

Figure 21:
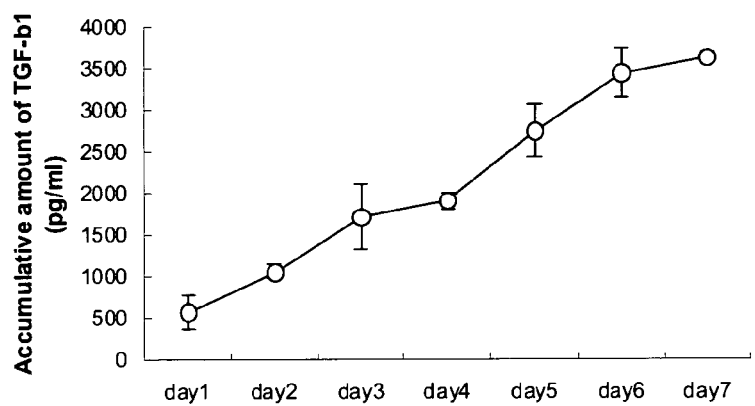

FIG. 21 shows the control release property of the gelatin microspheres with a cross-linking density of 5%. In this example TGF-β1 has been used as a probe instead of FITC.

FIG. 22A shows a side view of a PDMS valve. The light grey layer at the top 600 is the PDMS cover layer of the channel and 610 is the PDMS channel. The layer 620 indicates the thin PDMS layer with the features of the valve. FIG. 22B shows the situation when the hollow valves are filled with air, they will hump up and block the microfluidic channel on top. Such a valve provides an effective system to control the flow of cultivation medium through the channel. FIG. 22C shows the AutoCAD® drawing used to manufacture the silicon template.

Figure 23:
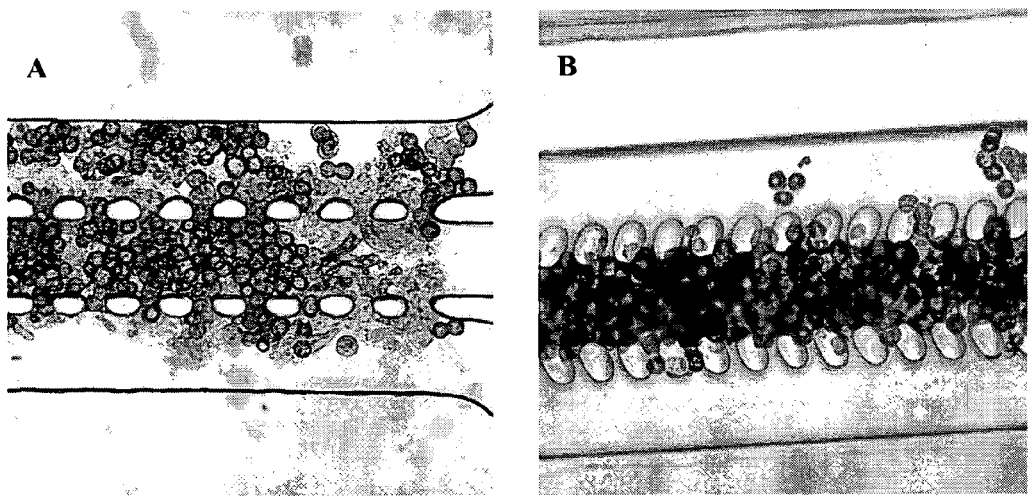

FIG. 23 shows two different geometrical designs of partitioning elements. FIGS. 23A and B show hepatocytes contained in a compartment at a cell density of $1.5 \times 10^6$ cells/ml. The cells were dynamically seeded into a microfluidic channel at 0.5 ml/h. FIG. 23A: 50 μm×30 μm semi-circular design; FIG. 23B: 30 μm×50 μm elliptical design.

Figure 24:
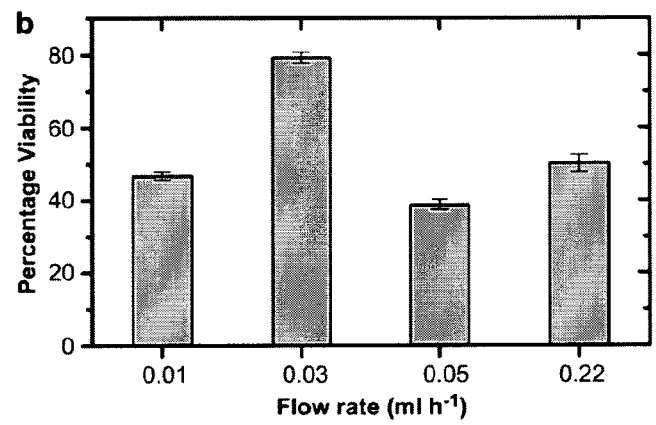

FIG. 24 shows the viability of cells in the compartment of a channel of a microfluidic flow device at different flow rates.

Figure 25:
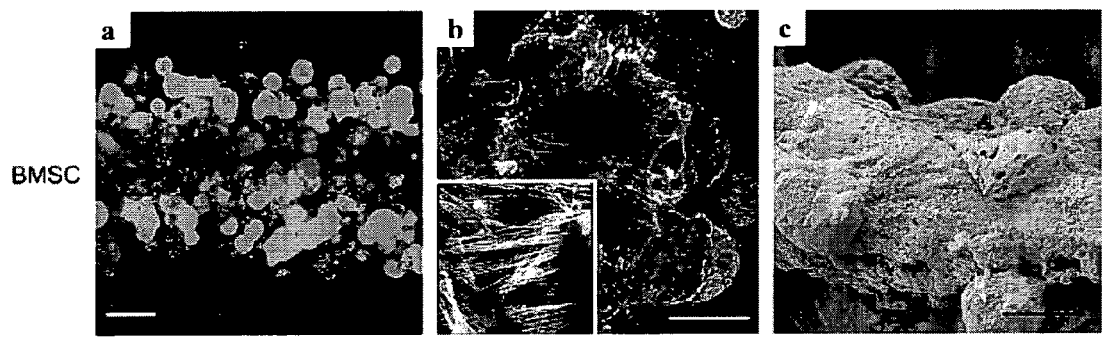

FIG. 25 shows that bone marrow mesenchymal stem cells (BMSC) in a compartment of a channel of a microfluidic continuous flow device are viable. It can further be seen that those cells are maintained in a 3D morphology after 3 days of perfusion culture. FIG. 25a shows a confocal image of BMSC stained with Calcein AM and propidium iodide indicated good cell viability. Scale bar: 50 μm. FIG. 25b shows a confocal image of F-actin staining which shows cells with cortical distribution of actin, reminiscent of the 3D cell morphology. In contrast, cells in 2D show extensive stress fiber formation (insets). Scale bar: 20 μm. FIG. 25c show a SEM image of cells illustrating rounded 3D cell morphology with gradual merging of cell-cell boundaries. Scale bar: 10 μm.

Figure 26:
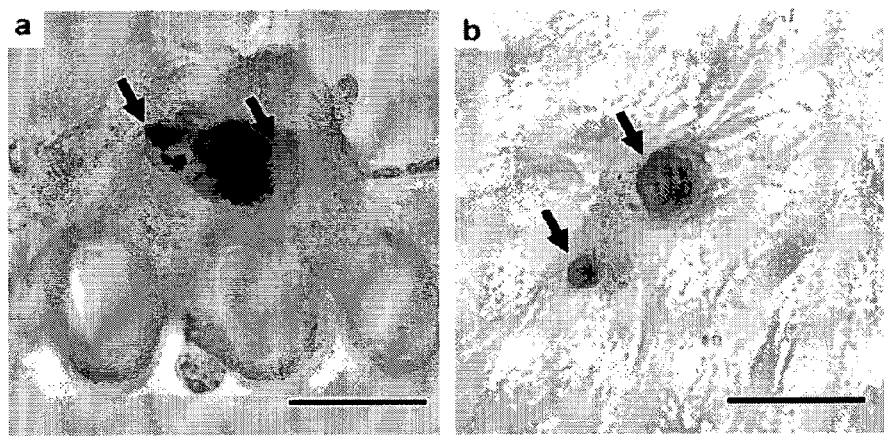

FIG. 26 shows primary bone marrow mesenchymal stem cells (BMSCs) which can be differentiated into osteoblasts in a compartment of a microfluidic continuous flow device after 1 week of osteogenic induction. FIG. 26a: von Kossa staining showed calcium salt deposition by BMSCs in a compartment of a microfluidic continuous flow device, similar to the staining obtained in a 2D monolayer control (FIG. 26b). Scale bar: 50 μm.

DETAILED DESCRIPTION OF THE INVENTION

In a first aspect the present invention refers to a microfluidic continuous flow device comprising:
   a channel comprising a first and a second area wherein the
      first area is a compartment which is defined by partitioning elements and the second area is a space outside the compartment;
      wherein through passages which are formed between the partitioning elements are dimensioned such as to retain a biological material and a sustained release composition, which are comprised in the compartment, within the compartment;
      wherein the sustained release composition is adapted to release at least one substance which supports cultivation of the biological material;
   wherein the channel has a first inlet for the compartment for introducing biological material into the compartment; a second inlet for introducing a cultivation medium into the space of the channel arranged outside of the compartment, and an outlet
      wherein the second inlet and the outlet are arranged such as to allow a flow of cultivation medium through the channel.

Such microfluidic continuous flow devices are employed, e.g., for high-throughput experimentations or to study cellular behavior in controlled conditions. In such a microfluidic continuous flow device a laminar flow environment can be created, thus, these devices can, e.g., be used to spatially control the positioning of soluble factors relative to cells. It has been demonstrated by Lama, M. T., Sima, S., et al. (2006, Biomaterials, vol. 27, p. 4340) that laminar flowing fluid can be used to pattern cells as well as their microenvironments. Laminar flow conditions are in general automatically created in microfluidic flow devices due to the microsize of the components used for such devices. This cell patterning technique is meaningful, for example, for stem cell research, where people can draw the relationship between microenvironments and cell fate. However, pattern cells by adjusting fluid flow may be coupled to fluid shear stress, and the environment experienced by the cells is uniform. To generate concentration gradients of substances, such as soluble factors on cells which support cultivation of biological material, gradient generators are incorporated into microfluidic devices to study the correlation between concentration and cell behavior. Usually, the gradients are generated by sequential merging or splitting of multiple inlet streams containing different substances which support cultivation of biological material (Dertinger, S. K. W., Chiu, D. T., et al., 2001, Anal. Chem., vol. 73, p. 1240). When designing these gradient generators, certain parameters have to be taken into consideration, such as transport phenomenon and shear stress. It requires a certain skill to design, fabricate and operate these integrated devices. To provide an alternative solution or additional option, the present invention provides a microfluidic continuous flow device in which sustained release compositions are confined at the center in a compartment together with a biological material, such as cells or cell aggregates. The sustained release composition releases soluble factors directly in the immediate surrounding of the biological material. The use of gradient generators or other external sources for these substances, such as soluble factors which support cultivation of biological material can thus be avoided.

Some biological materials, such as endothelial cells, require shear forces to develop properly (Nerem, R., Alexander, R., et al., 1998, Am. J. Med. Sci., vol. 316, no. 3, p. 169). Therefore, the through passages in the wall (see e.g. FIG. 9, space between the partitioning elements) are dimensioned such as to retain biological material in the compartment. To "retain" means that the biological material and/or a sustained release composition cannot pass between the partitioning elements. However, the through passages allow flow of cultivation medium introduced into the space outside of the compartment into the compartment and at the same time outflow of cultivation medium out of the compartment (indicated in FIG. 9 by bend arrow). By changing the distance between the partitioning elements the inflow and thus the shear forces on the material inside the compartment can be adjusted to meet the requirements of the biological material inside the compartment.

However, other cells are more sensitive to shear forces and do not grow as in their natural in vivo environment when exposed to shear stress. Therefore, to avoid shear forces on the biological material confined in the compartment, in another aspect the through passages in the wall (see e.g. FIG. 9, space between the partitioning elements) are dimensioned such as to allow through passage of molecules into and out of the compartment only by diffusion (indicated in FIG. 9 by bend arrow). "Diffusion" generally refers to the passive transport of molecules from a place of higher concentration to a place of lower concentration along a concentration gradient. Driving force for diffusion is the random motion of molecules as a result of intermolecular collisions (Brownian motion). Limiting the distance between the partitioning elements to an extent that only diffusion of molecules in and out of the compartment but no liquid flow is possible, allows to avoid any shear forces on the biological material comprised in the compartment.

The molecules which can enter and exit the compartment by diffusion can be gases, such as $N_2$, $O_2$ and $CO_2$ or non gaseous substances (nutrients) which are contained in the cultivation medium and which are helpful or needed for cultivation of biological material confined in the compartment. Cultivation medium, culture medium or growth medium is a fluid or liquid designed to support the growth and/or differentiation of biological material confined in the compartment. In general it is differentiated between two different kinds of cultivation medium. Those used for cell culture, which use specific cell types derived from plants or animals, and microbiological culture, which are used for growing microorganisms, such as bacteria or yeast. The most common growth media for microorganisms are nutrient broths; specialized media are sometimes required for microorganism and cell culture growth. Such media are known to a person skilled in the art and depend on the biological material that one wishes to culture in the compartment of the microfluidic continuous flow device.

Some of the most common culture medium used for example for eukaryotic cells include, but are not limited to RPMI 1640, DMEM, F12K, Basal Salt Mixtures, Dulbecco's Media, Ham's Nutrient Mixtures, MCDB Media, MEM Media, Medium 199, MegaCell™ Media, Ames' Media, BGJb Medium (Fitton-Jackson Modification), Click's Medium, CMRL-1066 Medium, Fischer's Medium, Glascow Minimum Essential Medium (GMEM), Iscove's Modified Dulbecco's Medium (IMDM), L-15 Medium (Leibovitz), McCoy's 5A Modified Medium, NCTC Medium, Swim's S-77 Medium, Waymouth Medium and William's Medium E.

It is also possible to include additional substances in the cultivation medium which are not necessary for the survival or growth of the biological material but for its development or differentiation into a specific direction, e.g. a specific cell type. It is for example a desire to control the development of stem cells in order to obtain a specifically differentiated cell type. To name only two examples, to differentiate bone marrow mesenchymal stem cells (BMSC) toward an osteogenic lineage, dexamethasone, ascorbic acid, and β-glycerophosphate are added to the cultivation medium. For neurogenic induction of bone marrow mesenchymal stem cells β-mercaptoethanol and a brain-derived neurotrophic factor is added to the cultivation medium.

In summary, all gases or substances mentioned above which are contained in the cultivation medium (including $H_2O$) can enter or exit the compartment via diffusion and liquid flow, respectively. Also all molecules not contained in the cultivation medium but originating from the biological material or any other material comprised in the compartment can exit the compartment via diffusion and liquid flow, respectively. Those molecules can be gases (such as $CO_2$) or substances released from the cells, such as enzymes, inorganic molecules or other metabolites.

To allow transport of molecules into and out of the compartment the partitioning elements can be evenly or unevenly spaced apart. In one example, the distance between the individual partitioning elements is between about 50 nm to about 30 μm. In one example, the distance between the partitioning elements is between about 1 μm to about 20 μm. In one example the distance between the partitioning elements is adapted to avoid migration of biological material, such as cells and/or cell aggregates out of the compartment. The narrowest width through which a cell or cell aggregate can migrate represents the threshold/minimum width size. It should be noted that through passages of non-uniform widths can be obtained with partitioning elements of different sizes, specifically different widths, instead of spacing the partitioning elements gradually further apart.

Figure 2:
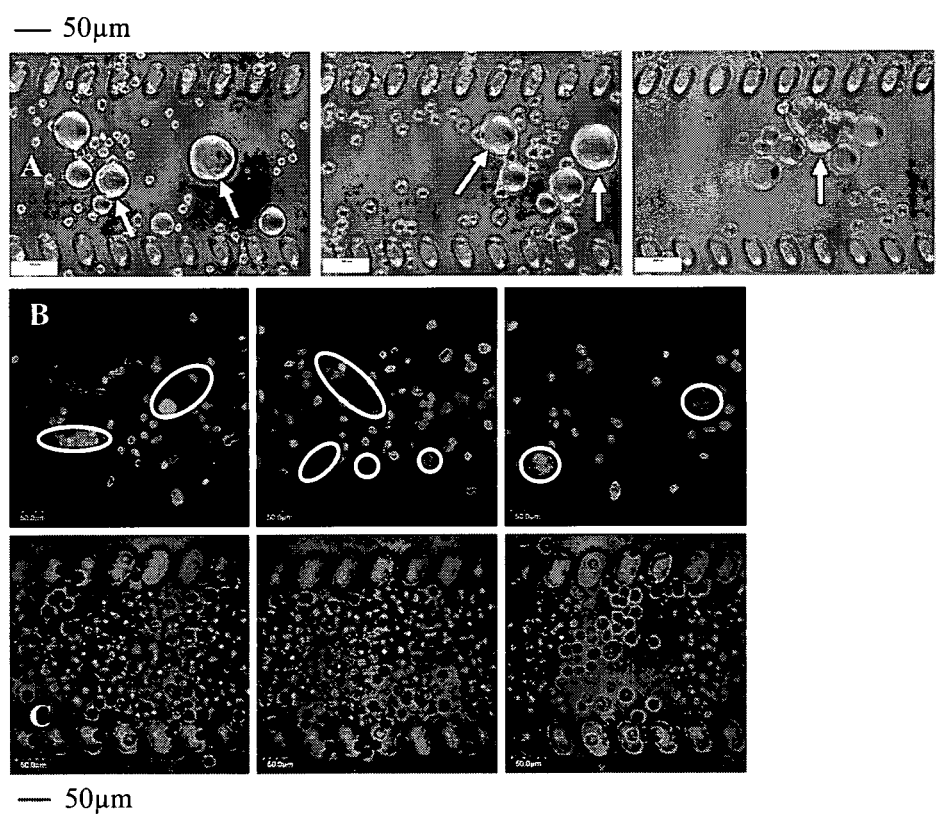

Although the partitioning elements are shown, for example in FIG. 2 to be pillars of an elliptical cross-section, partitioning elements having other cross-sections of regular or irregular shapes are also possible. Such other shapes include a rectangular or a trapezoid. In another example, the partitioning elements may have a semi-circular (see FIG. 23A), circular, or triangular cross sections or an elongated cross section. Partitioning elements of other polygonal cross-sections, such as a square, hexagonal, pentagonal, octagonal etc. and other shapes are also possible. It is also possible that neighboring partitioning elements are connected at their bases with each other and would then be more similar to a wall having wholes instead of stand-alone partitioning elements.

It is also contemplated that the vertical profile of a partitioning element does not necessarily need to be uniform along its entire height, but can vary from the base to the top of the partitioning element. Examples of such a shape include a semi-circle, triangle, trapezium or square pyramid, or a cone.

In one example, an array of partitioning elements such as 30 elliptical micropillars can be used to define a compartment wherein each micropillar is about 30×50 µm in size. In this array of micropillars the distance between the micropillars is about 20 µm. The size of the partitioning elements and the distance between the partitioning elements depends largely on the biological material to be retained in the compartment of the microfluidic continuous flow device and can thus vary over a wide range. As mentioned before the distance between the partitioning elements also depends on the question whether a flow of medium into the compartment is desired or not, i.e. flow in of medium or molecule transport in and out of the compartment only via diffusion.

The partitioning elements define or delimit the compartment which comprises the biological material. In general, whether the compartment is defined entirely by the partitioning elements or partly also by other elements of the channel depends on the location of the compartment within the channel. As shown for example, in FIG. 10A one side of the compartment on the left side is defined by the first inlet 140 through which the biological material is introduced into the compartment 180. The compartment 180 in FIG. 10A on the left side is arranged within the channel in such a way that a space 190 is created in the channel on either side of the compartment. Due to the fact that the cultivation medium can access the inside of the compartment from two sides, supply of the biological material within the compartment is enhanced.

However, as shown in FIG. 10B it is also possible that the space 190 outside the compartment 180 is arranged on one side of the compartment only, i.e. the compartment is defined at three sides by the circumferential wall of the channel and the other side facing the area outside the compartment is defined by partitioning elements 150.

The top cover layer and bottom cover layer of a channel form in general also the top and bottom of the compartment arranged inside the channel as can be seen in the top view in FIG. 1.

As already mentioned, the first inlet through which biological material is introduced into the compartment is also an element of the channel which can define a part of the compartments circumferential perimeter (see e.g. FIG. 23A). However, it is also possible that the first inlet 140 is arranged in the top or bottom cover layer of the channel as illustrated in FIG. 10A for the second compartment located in the right part of the channel. In this case the entire compartment is defined by the partitioning elements.

In general the first inlet for the compartment can be arranged anywhere along the compartment as long as it ensures proper introduction of the biological material in the compartment of the channel. In one example, the first inlet is arranged at the side of the compartment being located nearest to the second inlet of the channel through which the cultivation medium is introduced into the channel as for example shown in FIG. 10A. In still another example the first inlet is arranged at a position along the longitudinal side of a long stretched, such as rectangular shaped, compartment. In still another example, the compartment does not include a first inlet at all. The first inlet for introducing the biological material can be omitted in case the biological material is introduced into the channel before the manufacture of the channel is completed, i.e. before the cover or bottom layer is added to close up the channel of the microfluidic continuous flow device.

The size and shape of the compartment follow in general the size and shape of the channel. However, in general the compartment can have any shape. While for example in FIGS. 10A and 10B the shape of the compartment follows the shape of the elongated rectangular channel it is also possible that the compartment lying in the channel has a curved shape or comprises a series of bends. In another example it would also be possible that the compartment has a round, elliptical or u-shape. With a u-shaped compartment it is meant that one side of the compartment is defined by a first inlet (see e.g. FIG. 8) or a wall of the channel while the remaining sides are defined or delimited by partitioning elements.

In the examples described herein the compartment has an elongated shape, i.e. the shape of the compartment is a long stretched rectangular or ellipsoid which extends along the entire length or almost the entire length of the channel.

As to the dimensions of the compartment, in general each compartment is dimensioned such that uptake and discharge of molecules from each compartment into and out of the cultivation medium is possible over the entire space of each compartment. This is desirable because supply of molecules comprised in the cultivation medium should be ensured for every biological material located inside the compartment. In case uptake and discharge in and out of the compartment is driven by diffusion the size of the compartment is limited by the metabolic demand of the biological material located inside the compartment. That means for example that it needs to be ensured that biological material, such as a cell located in the center of the compartment, which requires a certain amount of oxygen per time is supplied via diffusion with enough oxygen to ensure sufficient function of the cell. Thus, depending on the biological material used the maximal dimensions of the compartment can vary. In one example, a compartment has at least in one dimension a width of maximal 200 µm. In one example the compartment has a rectangular or u-shape with a width between about 10 µm to about 200 µm. Such a compartment can extend through the channel over a length between about 400 µm to about 1 to 10 cm. In case the size of the through passages between the partitioning elements allows transport of molecules in and out of the compartment only by diffusion, the compartment can have a maximal width of 200 µm and a minimum width which is at least two times the diameter of the biological material, such as cells, retained in the compartment.

The volume of a compartment is variable and can be adapted to the desired application. In one example the volume of the compartment can vary between about 3 nl to 100 nl. In another example the volume is between about 5 nl to about 20 nl.

In another example, at least one of the channels comprises at least two compartments wherein each compartment has a first inlet for introducing biological material into the compartment as shown for example in FIG. 10A. In case a channel comprises more than one compartment the compartment can be of the same shape or have different shapes. In addition, it is also possible that the compartments comprise the same or different biological material.

In case a channel comprises more than one compartment those compartments can be arranged in a row as shown in FIG. 10A or they can be oriented parallel to each other wherein in such a case those two parallel compartments would be arranged to leave a space between them in order to allow cultivation medium to flow between both compartments.

The size of the compartments also depends on the size of the channel of the microfluidic continuous flow device. The channel may have a length between about 50 mm to about 10 cm, a height between about 20 µm to about 500 µm and a width between about 100 µm and 1000 µm. In one example, the width of the channel is about 600 µm. A channel having a width of about 600 µm may comprise for example a compartment located in the center of the channel and having a width of 200 µm. The space left between the wall of the channel and the compartment has a width of 200 µM on both sides of the compartment. In another example a channel is about 1.5 cm long and has a height of about 100 µm.

The space outside the compartment takes up the whole space of the channel which is not occupied by the compartment. The absolute size of the second area which is the space outside the compartment is not essential for the cultivation of the biological material inside the compartment and can thus vary over a wide range.

Depending on the shape, size and location of the compartment the space can be an interconnected space as shown in FIG. 10A or can be separated or almost be separated by a compartment into two areas as shown for example in FIG. 8. Thus, the dimension of the space outside the compartment is determined by the size of the channel and the size of the compartment(s) located inside the channel. The size of the space can be evenly or unevenly distributed on both sides of the compartment. For example, the space on the right and the left side in FIG. 9 is evenly distributed. The width of the space on each side of the compartment can be between about 10 µm to about 500 µm or 400 µm. In one case it has a width of about 200 µm. The width of the space 190 shown in FIG. 10B which is located only on one side of the compartment is also variable. It can have a width for example between about 10 µm to about 500 µl or 400 µm. In one example the width is about 200 µm.

Although the channels are shown, for example in FIG. 8 to be channels of a rectangular cross-section (the part between the second inlet and the outlet), channels having other cross-sections of regular or irregular shapes are also possible. Such other shapes include a rectangular or a trapezoid. In another example, a channel can have a semi-circular cross section. A channel having another polygonal cross-section, such as a square, hexagonal, pentagonal, octagonal etc. or any other shape is also possible. A microfluidic continuous flow device having more than one channel can comprise channels having different cross-sections.

In another aspect, the channel further comprises a medium flow separator, wherein the medium flow separator is arranged between the end of the compartment located in the direction of the outlet of the channel and the channel outlet. In another example, the medium flow separator can be located also or in addition between the beginning of the compartment located in the direction of the second inlet of the channel and the channel inlet. The shape of the medium flow separator is highly variable and can have any shape as long as it allows splitting the medium flow inside the channel to guide it through the space outside of the compartments located in the channel. A medium flow separator located near to the second inlet of a channel further avoids that the incoming flow of cultivation medium directly hits the partitioning elements defining the compartment and thus avoids the creation of shear forces in the compartment created by the pressure of the incoming stream of cultivation medium on the compartment.

In case a channel comprises more than one compartment it is also possible to locate a medium flow separator between the compartments comprised in the channel. When referring for example to FIG. 10A that would mean that a second medium flow separator in addition to the medium flow separator 145 located at the inlet of the channel is located between the first and the second compartment shown in FIG. 10A which would result in keeping the flow of cultivation medium separate in the space 190 formed on both sides of the compartments 180 shown in FIG. 10A.

For example, in FIG. 8 a medium flow separator 145 and the first inlet 140 for introduction of biological material are lying in the same plane. The first inlet 140 is incorporated as part of the medium flow separator 145. The medium flow separator 145 splits the incoming stream of cultivation medium into two streams and guides them into the space 190 outside the compartment 180. FIG. 8 also shows a medium flow separator arranged between the end of the compartment located in the direction of the outlet of the channel and the channel outlet 170. A medium flow separator located in such a position can also be described as medium flow fuser as the medium flowing in the space outside the compartment on both sides of it fuses into one cultivation medium stream after passing the medium flow separator.

The medium flow separators can have a round shape, an elliptical, an oval, a rectangular shape or a wedge-shape. FIG. 8 shows an example of a channel comprising a medium flow separator 170 having a wedge-shape. This wedge-shaped medium flow separator 170 separates the two cultivation medium streams flowing in the space 190 on the right and left side of the compartment 180. At the end of the wedge-shaped medium flow separator 170 both cultivation medium flows are unified again and exit the channel 195 through the outlet 120 connected to the channel 195 via the outlet channel 130.

The medium flow separator can be of variable size as can be seen for example in FIG. 8. The size depends on its position and shape. In general a medium flow separator lying within the channel, such as the medium flow separator 170, normally has a width which does not exceed the width of the compartment inside the channel which is about 200 µm. However, in other examples the width of a medium flow separator lying inside the channel can be between about 50 µm to about 400 µm.

A medium flow separator located at the inlet of a channel, such as the round medium flow separator 145 shown in FIG. 8, can have a width which is equal the width of the compartment or exceeds the width of the compartment. For example, the round medium flow separator 145 can have a width or diameter which equals the width of the whole channel, i.e. a width between about 100 µm and 1000 µm. In another example the width or diameter of the round flow separator is between about 50 to 400 µm and in still another example the width or diameter of the round medium flow separator is about 200 µm.

The second inlet and the outlet of the channel are in general arranged to allow a flow of the cultivation medium over the entire length of the channel irrespective of the shape of the channel. Other than for example the microfluidic flow device referred to in Toh, Y.-C., Zhang, C., et al. (2007, Lab on a Chip, vol. 7, p. 302) the microfluidic flow device of the present invention (see for example FIG. 8) comprises only one outlet and one second inlet.

In case a channel comprises more than one medium flow separator the shape of them can be the same or different. An example is illustrated in FIG. 8. The medium flow separator located near the second inlet of the channel has a round shape while the medium flow separator located before the outlet has a wedge-shape.

The substrate for manufacturing the channels may be molded using any type of material which can be made into a microfluidic continuous flow device of the invention. In one aspect the material is chosen to allow observation of the biological material. In another example only a part of the channel is made of a transparent material which allows observation of the biological material inside the compartment. Such materials include polymers, glass, silicone or certain types of metal. In one embodiment, the material for forming the substrate is a biocompatible material. Biocompatible material includes, but is not limited to, glass, silicon and a polymerisable material. The polymerisable material includes, but is not limited to, monomers or oligomeric building blocks (i.e. every suitable precursor molecule) of polycarbonate, polyacrylic, thick-photo resist epoxy resin (SU-8 series from MicroChem. Inc., MA, US) polyoxymethylene, polyamide, polybutylenterephthalate, polyphenylenether, polydimethylsiloxane (PDMS), mylar, polyurethane, polyvinylidene fluoride (PVDF), fluorosilicone or combinations and mixtures thereof. In some embodiments, the biocompatible material comprises PVDF and/or PDMS. Advantages of PVDF and PDMS are their cheap price and superior biocompatibility. In addition, they have high gas permeability, a characteristic which is important in closed microdevices as it facilitates the permeation of supplied oxygen to the cell culture in order to ensure cell respiration. Furthermore, as they are transparent, they conveniently allow direct morphological observation of the cells under an observation device, e.g. a microscope, to be carried out (see for example FIG. 2). In one example the microfluidic continuous flow device is made of poly(-dimethylsiloxane) (PDMS).

Furthermore, the microfluidic continuous flow device comprises a cover layer forming the top of the channel. The cover layer can have any suitable optical transparency. A fully opaque cover or one which is transparent, or one which is translucent material (thereby permitting the transmission of a certain amount of light), may all be used. In a further embodiment, the cover may comprise a biocompatible material that is transparent or at least substantially translucent in order that the device is compatible for use with optical microscopes which can provide a backlight that can be directed through the device in order to provide a bright view of the processes occurring in the device during its use.

Instead or in addition to an optical observation of the biological material in the compartment of a channel it is also possible to carry out a chemical analysis of the cultivation medium which passed through the channel and exits it via the outlet.

Another aspect of the invention concerns the fabrication of the above described microfluidic continuous flow devices. The template for creating the device of the invention can be fabricated according to any technique known in the art, such as photolithography, etching, electron-beam lithography, laser ablation, hot embossing, etc. depending on the material used. For example, when fabricating devices using Si templates in microscale and nanoscale, it is possible to use laser ablation, etching or hot embossing, and electron-beam lithography respectively. The above techniques are known in the area of microelectronics and microfabrication. After creating the template the microfluidic continuous flow device is then created by replica molding poly(-dimethylsiloxane) (PDMS) or some other polymer on the template. In one example, the silicon templates can for example be fabricated by standard deep reactive ion etching (DRIE) process.

The flow of cultivation medium through the channel of the microfluidic continuous flow device of the invention can be varied. The flow rate can be between about 20 µl/h to about 500 µl/h. In case the biological material inside the compartment is sensitive to shear stress the flow rate of cultivation medium through the channel can be between about 30 µl/h to about 220 µl/h. The flow rate is constant or may be changed during the cultivation time of the biological material inside the channel. In one illustrative example the flow rate is about 30 µl/h. In order to simulate physiological flow conditions, the delivery of cultivation medium and control of cultivation medium flow in the present device can be achieved with any technique known in the art. One method is to adjust the height of the cultivation medium reservoir. This would correspondingly adjust the hydrostatic pressure, and thus the flow rate of the fluid medium in the device. Alternatively, the flow rate can be adjusted by use of an actuating device e.g. a pump. One or more pumps may be incorporated into the device according to any known microfabrication technique. Examples of pumps which may be used include micromachined pumps, syringe pumps, diaphragm pumps, reciprocating pumps and other pumping means known to those skilled in the art. It is also possible to induce the flow of cultivation medium through a channel via capillary action. In one example shown in FIG. 17A the flow of cultivation medium through the channel is driven by syringe pumps 510 which are used to withdraw the cultivation medium out of the channels 530, which means that those pumps create a negative pressure which drives the cultivation medium flow.

As the phrase "microfluidic continuous flow device" indicates, the flow of the medium through the channel is continuous. A continuous flow of cultivation medium through the channel is provided to ensure proper supply of the biological material inside the compartment with all necessary substances for cultivation and development of the biological material.

The biological material which can be introduced and cultivated in the channel of the microfluidic continuous flow device includes, but is not limited to prokaryotic cells, eukaryotic cells, cell aggregates from the aforementioned group of cells and mixtures thereof.

The group of prokaryotic cells includes, but is not limited to archaea, green bacteria, gram-positive bacteria, deinococcus, spirochaeta, planctomycetes, *Chlamydia*, purple bacteria including the group of gram-negative bacteria, cyanobacteria and flavobacteria. (Systematic classification is based on the 16S-rRNA comparison as referred to by Hans G. Schleger, 1992, Allgemeine Mikrobiologie, $7^{th}$ edition, page 93). Examples for eukaryotic cells include, but are not limited to mammalian cells, ciliate cells, fungi, plants, flagellates and microsporidias.

Examples for mammalian cell lines or primary cells can include, but are not limited to bone marrow stroma cells, calvarial osteoblasts, Langerhans cells, hepatocytes, chondrocytes, sinusoidal endothelial cells, cardiomyocytes, glioma cells (from brain), dermal fibroblasts, keratinocytes, oligodendrocytes, hematopoetic stem cells, T-lymphocytes, macrophages and neutrophils. Primary hepatocytes or primary kidney cells can also be used. Stem cells, cancerous cells as well as non cancerous cells can also be used as biological material. Some examples of cell lines which can be used are primary adipocytes, A549 lung cells (carcinomic human alveolar basal epithelial cells), proximal tubular human kidney HK-2 cells and the human hepatocellular carcinoma cell line HepG2/C3A (liver). Besides cells of human origin, cells of cat, cow, rat, mouse, sheep, monkey, pig, horse, dog and amphibian origin and insect cells can also be used. Of particular interest are cells or cell lines which can be used for drug tests.

Cell aggregates refer to a cluster of cells which is isolated from a biological tissue or to cell aggregates which are obtained artificially. A "tissue" is in general considered as a group of related cells which are joined together. The cells in a tissue are not identical, but they work together to accomplish specific functions. In cell-dense and matrix-poor tissues of the internal organs, cells support one another via cell-cell interactions, supplemented by small amount of the extracellular matrices (ECM) secreted by the cells. It is a further object of the present invention to post form such structures in the channel of the microfluidic continuous flow device. It is known that cells cultured in a three dimensional environment which mimic the in vivo display gene expression profiles and biological activities that resemble the in vivo situation more closely than the cells cultured in a two dimensional monolayer (Abbott A., 2003, Nature, vol. 424, no. 6951, p. 870).

One way to mimic this in vivo environment also in the channel of the microfluidic continuous flow device is to form artificial cell aggregates. One way to form cell aggregates is to modify the cell surface to generate reactive target sites for ligation of single cells. Various methods for cell surface modification are known in the art. Among them are genetic, enzymatic or chemical strategies (Greenberg, M. E. et al., 1984, PNAS, vol. 81, no. 3, p. 969). Some people transfect the rat cerebral cell lines with neural cell-adhesion molecules (N-CAM) to encourage cellular aggregation (Medof, M. E. et al., 1996, Faseb J., vol. 10, no. 5, p. 574), and some paint the cell surface with exogenously added GPI-anchored proteins of interest (Kellam, B. et al., 2003, Chem. Soc. Rev., vol. 32, no. 6, p. 327). Another approach is via chemical modification of cell surface molecules. For instance, exogenous galactose oxidase can be applied to oxidize terminal galactosyl residues to generate ketone groups on cell surfaces (Kellam, B. et al., 2003, Chem. Soc. Rev., vol. 32, no. 6, p. 327). In another approach mammalian cells are surface engineered to present non-native functional groups, such as aldehyde (Kellam, B., De Bank, P. A., et al. 2003, Chem Soc Rev, vol. 32, p. 32'7), which can then react with the inter-cellular linkers, such as avidin-biotin-hydrazide (De Bank, P. A., Hou, Q., et al., 2007, Biotechnology Bioeng, vol. 97, no. 6, p. 1617) or polyethyleneimine hydrazide (PEI-hydrazide). The latter one is a transient polymeric inter-cellular linker with multiple hydrazide handles on a polyethylenimine (PEI) backbone which react with aldehyde functional groups on cell surfaces, modified by sodium periodate ($NaIO_4$), to induce cellular aggregation (FIG. 19). This product is referred to as PEI-hydrazide, PEI-hy (Ong, S. M., He, L., et al., 2007, Biomaterials, vol. 28, no. 25, p. 3656). Being a polymer of low molecular weight (MW~2000 KDa), the PEI-hy does not pose mass transport difficulties that bulk biomaterials like hydrogels and scaffolds do.

In another example dendrimer hydrazides are used as multivalent transient inter-cellular linkers (Zhao, D., Ong, S.-M., Dendrimer hydrazides as multivalent transient inter-cellular linkers, Biomaterials, epub 12 Jun. 2008). Thus, in one aspect the present invention is directed to a microfluidic continuous flow device comprising cells located in the compartment of the channel, wherein the cells comprise an inter-cellular linker. The intercellular linker can include, but is not limited to PEI-hy, ketone groups, cell-adhesion molecule (N-CAM), dendrimer hydrazides, GPI-anchored proteins or mixtures thereof.

Another option to mimic the in vivo extracellular matrices (ECM) of the biological material to be cultivated in the channel of the microfluidic flow device more closely is to embed the biological material in polyelectrolytes. Polyelectrolytes react by complex coacervation to form a polymer complex which polymer complex forms a three dimensional polymer matrix that can be perfused by liquids and is permeable to substances necessary to sustain the normal metabolic functions of the cells embedded therein and to products released by the cells. In general, for complex coacervation of polyelectrolytes two oppositely electrically charged polymers are required.

Both, naturally occurring and modified polymers are suitable for use as charged polymers. In this connection it is noted that the term "electrically charged" means that the polymers carry a net charge, i.e., are either positively or negatively charged, when present in a solution. The polymers which can be used are typically water soluble and biodegradable and in addition usually have a molecular weight of at least 10 kDa. Polyelectrolyte's can be introduced into the channel of the microfluidic continuous flow device together with the cells to be embedded therein or before introducing the cells.

Examples of polymers that can be used include, but are not limited to chitosan, polyanionic alginate, positively charged collagen, negatively charged collagen polyanionic alginate, $Ca^{2+}$, or synthetic polymers such as polycationic poly(L-lysine) and co-polymers or terpolymers that include poly (acrylic acid), poly(methacrylic acid), poly(methacrylate) or poly(methyl acrylate) to name only a few.

A useful terpolymer may consist of two polymer blocks containing at least one of acrylic acid and methacrylic acid and at least one of hydroxyethyl methacrylate and hydroxylpropyl methacrylate. Such terpolymers may consist of about 10%-50% hydroxyethyl methacrylate, about 10%-50% methacrylic acid and about 50% methyl methacrylate (HEMA-MAA-MMA). An example for such a terpolymer consists of 25% hydroxyethyl methacrylate, about 25% methacrylic acid and about 50% methyl methacrylate (HEMA-MAA-MMA) (Chia et al., 2000, Tissue Engineering, vol. 6, no. 5, p. 481). In another example the terpolymer consists of 25% hydroxyethyl methacrylate, about 50% methacrylic acid and about 25% methyl methacrylate (HEMA-MAA-MMA). Other terpolymers that can be used are described by Shao Wen et al who used terpolymers of different compositions for embedding living cells (Wen, S., Xiaonan, Y. and Stevenson, W. T. K., 1991, Biomaterials, vol. 12, p. 3'74; Shao Wen, Alexander, H., et al., 1995, Biomaterials, vol. 16, p. 325). These terpolymers consist of HEMA-MMA-MAA or HEMA-MMA-DMAEMA (cationic 2-(dimethylamino)ethyl methacrylate) whereas the latter terpolymer is positively charged.

Combinations of polymers from the aforementioned group can be used to form a polymer matrix for embedding living cells in a polymer matrix. Exemplary combinations of polymers in which a first charged polymer is reacted with a second charged polymer include, but are not limited to the following: chitosan—negatively charged terpolymer, polyanionic alginate—$Ca^{2+}$, positively charged collagen—negatively charged terpolymer, negatively charged collagen—positively charged terpolymer (Wen, S., Xiaonan, Y. and Stevenson W. T. K., 1991, supra), polyanionic alginate—polycationic poly (L-lysine).

Since polymers such as collagen are in their natural form neither positively nor negatively charged they need to be modified for use in the present invention. Techniques to modify such polymers are known in the state of the art. Chia et al. for example (2000, supra) describe cationic collagen obtained by esterification of the carboxyl groups with low-molecular-weight alcohol. Negatively charged collagen can, for example, be obtained by the method described by Donald G. Wallace and Joel Rosenblatt (2003, Advanced Drug Delivery Reviews, vol. 55, p. 1631). Other examples of an uncharged polymer that can be modified to carry an electrical net charge include, but are not limited to poly (vinyl alcohol) and further polysaccharides such as dextrans and polysaccharides of the carrageenan family (obtained from the red seaweeds).

Optionally, polymers that are naturally charged can be modified to (better) match the electrical charge of the oppositely charged polymer that is used as reaction partner for complex coacervation. The different electrical charge can also be used to influence the permeability of the polymer matrix. Large differences in charge densities between the oppositely charged polymers tend to make the membrane more permeable.

Using complex coacervation ECM like matrices can be composed. As it is known in the art, complex coacervation can be effectively controlled, for example by varying the molecular weight, the charge density and the concentration of the charged polymers as well as the reaction time of the oppositely charged polymers in the channel. The permeability and transport properties of the polymer membrane can be modulated depending on the requirement of the biological material embedded therein (see e.g. US-2006-0019361-A1).

When embedding the biological material in the compartment of a channel in a polymer it is also possible to extend the distance between the partitioning elements. When embedded in a polymer the biological material will not pass through the through passages between the partitioning elements even though the diameter of the biological material might in some cases be smaller than the distance between the partitioning elements defining the compartment.

Another possibility to localize the cells within the compartment of the channel is to coat the surface of the compartment with a capture molecule. Therefore, in one aspect of the present invention at least a part of a surface of the partitioning elements, and/or the bottom and top of each of the channels lying within the compartment and/or the circumferential wall defining a part of the compartment are coated with at least one capture molecule. The use of capture molecules can support immobilization of the cells and thus the formation of cell aggregates which are able to form an ECM like structure. In one example, capture molecules include, but are not limited to monoclonal or polyclonal antibodies, binding fragments of antibodies, aptamers or mixtures of the aforementioned molecules. In another example, the capture molecules include, but are not limited to antibodies, binding fragments of antibodies or mixtures of the aforementioned molecules. It is also possible to use the inter-cellular linker as capture molecules. The inter-cellular linker can also be coated to the surface of the partitioning elements, and/or the bottom and top of each of the channels lying within the compartment and/or the circumferential wall defining a part of the compartment.

A first example of a capture molecule is an immunoglobulin (antibody), a fragment thereof or a proteinaceous binding molecule with immunoglobulin-like functions. Examples of (recombinant) immunoglobulin fragments include, but are not limited to $F_{ab}$ fragments, $F_v$ fragments, single-chain $F_v$ fragments (scF$_v$), diabodies, triabodies (Iliades, P., et al., 1997, FEBS Lett., vol. 409, p. 437), decabodies (Stone, E., et al., 2007, Journal of Immunological Methods, vol. 318, p. 88) and other domain antibodies (Holt, L. J., et al., 2003, Trends Biotechnol., vol. 21, no. 11, p. 484). An example of a proteinaceous binding molecule with immunoglobulin-like functions is a mutein based on a polypeptide of the lipocalin family (WO 03/029462, Beste et al., 1999, Proc. Natl. Acad. Sci. USA, vol. 96, p. 1898). Lipocalins, such as the bilin binding protein, the human neutrophil gelatinase-associated lipocalin, human Apolipoprotein D or glycodelin, posses natural ligand-binding sites that can be modified so that they bind to selected small protein regions known as haptens. Examples of other proteinaceous binding molecules are the so-called glubodies (see e.g. international patent application WO 96/23879 or Napolitano, E. W., et al., 1996, Chemistry & Biology, vol. 3, no. 5, p. 359), proteins based on the ankyrin scaffold (Mosavi, L. K., et al., 2004, Protein Science, vol. 13, no. 6, p. 1435) or crystalline scaffold (e.g. internation patent application WO 01/04144) the proteins described in Skerra, J. 2000, Mol. Recognit., vol. 13, p. 167), AdNectins, tetranectins and avimers. Avimers contain so called A-domains that occur as strings of multiple domains in several cell surface receptors (Silverman, J., et al., 2005, Nature Biotechnology, vol. 23, p. 1556). Adnectins, derived from a domain of human fibronectin, contain three loops that can be engineered for immunoglobulin-like binding to targets (Gill, D. S. & Damle, N. K., 2006, Current Opinion in Biotechnology, vol. 17, p. 653). Tetranectins, derived from the respective human homotrimeric protein, likewise contain loop regions in a C-type lectin domain that can be engineered for desired binding (ibid.). Peptoids, which can act as protein ligands, are oligo (N-alkyl) glycines that differ from peptides in that the side chain is connected to the amide nitrogen rather than the α carbon atom. Peptoids are typically resistant to proteases and other modifying enzymes and can have a much higher cell permeability than peptides (see e.g. Kwon, Y.-U., and Kodadek, T., 2007, J. Am. Chem. Soc., vol. 129, p. 1508). If desired, a modifying agent may be used that further increases the affinity of the respective capture molecule for any or a certain form, class etc. of analyte molecules.

Another group of capture molecules that can be used are aptamers. Aptamers are specific RNA or DNA oligonucleotides which are typically 15-40 nucleotides long or proteins typically comprised of 10 to 20 amino acids which can adopt a vast number of three dimensional shapes. Due to this property, aptamers can be produced to bind tightly to a specific molecular target. Because an extraordinary diversity of molecular shapes exist within all possible nucleotide sequences, aptamers can be obtained for a wide array of molecular targets, including most proteins, carbohydrates, lipids and nucleotides. Aptamers are generally produced through an in vitro evolutionary process called "systematic evolution of ligands by exponential enrichment" (SELEX). The method is known in the art and is an iterative process based on selection and amplification of the anticipated tight binding aptamer. In addition to high specificity, aptamers have very high affinities to their targets. Typically aptamers generated against proteins have affinities in the picomolar to low nanomolar range (Bunka, D. H. J. and Stockley, P. G., 2006, Nat. Rev. Microbiol., vol. 4(8), p. 588; Carothers J M, Oestreich S C, et al., 2004, J Am Chem. Soc., vol. 126(16), p. 5130; Hoppe-Seyler F, Butz K, 2000, J Mol. Med., vol. 78(8), p. 426).

The use of different kinds of capture molecules allows to specifically localize the biological material in different sections of the compartment of a channel of the microfluidic continuous flow device. For example, in case different kinds of biological material, such as different cell types, are introduced into the compartment of a channel those cell types can be localized in different order within the channel in order to rebuild the natural in vivo pattern.

The use of capture molecules for binding of the biological material also allows introducing biological material into the compartment which would otherwise due to its size pass through the through passages between the partitioning elements.

It is also possible to combine the aforementioned methods, such as the use of capture molecules, linkers and polymer matrix to support formation of an in vivo like microenvironment within the compartment of a channel. However, it should be noted that the microfluidic continuous flow device of the present invention can also be used without using capture molecules, inter-cellular linkers or polymer matrices. The aforementioned means can be used for specific applications but as shown in the experimental section biological material such as eukaryotic cells is viable and can grow and differentiate within the channel of the device once seeded into it even without the use of capture molecules, inter-molecular linker or polymer matrices. Another possibility to support the growth and development of biological material enclosed in the compartment is the use of sustained release compositions which release at least one substance which supports cultivation of the biological material.

Controlled release can address several problems with regard to sustained delivery of substances, such as pharmaceuticals, inorganic molecules or proteins in a convenient and controllable manner, so that chemical change or denaturation during storage can be avoided. The half-lives of some soluble factors, such as growth factors are very short, ranging from several minutes to an hour. Thus, encapsulating them into carriers and control releasing them is the ideal way to prevent, for example denaturation.

The use of sustained release compositions can also support the control of the microenvironment in the compartment of a channel of the microfluidic continuous flow device of the present invention. Introduction of sustained release compositions together with biological material avoids the use of external gradient generators for introduction of different compositions which are prudent for the development and grow of the cells in the compartment via the cultivation medium. Using a mixture of different sustained release compositions which release their respective substances at different time allows further to ensure supply of different substances at different times during growth and development/differentiation of the cells.

Sustained release compositions used in the device of the present invention can be made of any available suitable material. Examples of such materials with sustained release properties include, but are not limited to solid lipid nanoparticles (SLN), gamma-polyglutamic acid, poly(ethylene glycol) (PEG), poly(glycolic acid), hyaluronic acid, poly(L-lactic acid) (PLLA) and its copolymers with glycolic acid (PLGA), natural materials, such as collagen, alginate and fibrin. Also the biodegradable polymers referred to above for the formation of a polymer matrix via complex coacervation can be used as material for the manufacture of sustained release compositions.

In one example gelatin is used as sustained release composition. Gelatin is a commonly used natural polymer which is derived from collagen. The isoelectric point of gelatin can be modified during the fabrication process to yield either a negatively charged acidic gelatin, or a positively charged basic gelatin at physiological pH. This theoretically allows electrostatic interactions to take place between a charged biomolecule and gelatin of the opposite charge, forming polyion complexes (Young, S., Wong, M., et al., 2005, J. of Controlled Release, vol. 109, p. 256).

The crosslinking density of gelatin hydrogels has been shown to affect their degradation rate in vivo, and the rate of biomolecule release from gelatin carriers has been shown to have a similar profile, suggesting that complexed gelatin/biomolecule fragments are released by enzymatic degradation of the carrier in vivo.

The isoelectric point of gelatin can be modified during its extraction from collagen to yield either a negatively charged acidic gelatin, or a positively charged basic gelatin. This allows for flexibility in terms of enabling polyion complexation of a gelatin carrier with either positively or negatively charged substances. For instance, acidic gelatin with an IEP of 5.0 should be used as a carrier for basic proteins in vivo, while basic gelatin with an IEP of 9.0 should be used for the sustained release of acidic proteins under physiological conditions.

Sustained release compositions made of gelatin are commonly manufactured as block hydrogel, porous gelatin block hydrogel or gelatin microsphere.

The fabrication of block matrices begins with the preparation of the gelatin aqueous solution, where the gelatin is dissolved in deionized water (5 g gelatin per 50 ml $H_2O$) at 60° C. A variety of crosslinkers are available for this application such as glutaraldehyde (GA) or a water-soluble carbodiimide (WSC). Once the desired crosslinking time has been reached, the crosslinking reaction is quenched within the newly formed hydrogels. If glutaraldehyde is used, then the hydrogels are immersed in an aqueous solution of glycine at 37° C. for 1 h to block residual aldehyde groups of glutaraldehyde, and then rinsed with water. If water-soluble carbodiimide is used for crosslinking, then the hydrogels are immersed in an aqueous solution of hydrochloric acid (pH 3.0) for 1 h and then washed with water to deactivate and remove any unreacted crosslinker.

A variety of shapes can be fabricated from these block hydrogels, ranging from disks, to cubes, or strips by punching out or cutting them using a knife. More complex shapes such as tubes can be formed by running the crosslinking reaction within a mold of the correct configuration. After thorough rinsing, the fabricated hydrogels are freeze-dried and sterilized in ethylene oxide gas.

High porosity controlled-release scaffolds can be manufactured by using the fundamental techniques of crosslinking, swelling, and lyophilization. Briefly, glutaraldehyde is added to an aqueous solution of gelatin and the mixture is poured into a polypropylene mold for 12 h at room temperature to allow for crosslinking. The hydrogel is then treated with an aqueous glycine solution to quench the crosslinking reaction and washed with double-distilled water. The swollen hydrogel is then frozen, allowing ice formation to act as a porogen. Scaffolds are then lyophilized with the help of a freeze dryer for 4 days to completely dry them. Scanning electron micrographs of porous gelatin hydrogels fabricated using this technique reveal uniform sized pores ranging in diameter from 45 to 250 µm depending on the method of freezing utilized. It has been shown that hydrogels frozen in liquid nitrogen have a two-dimensionally ordered structure, while those placed in −20° C. freezers have larger pores and a three-dimensional, interconnected structure, suggesting that the porosity of these constructs can be controlled by the size of ice crystals formed during the freezing process.

Gelatin microspheres can be produced via glutaraldehyde crosslinking of a gelatin aqueous solution in a water-in-oil emulsion technique. In order to create the water-in-oil emulsion, an aqueous solution of gelatin (10 wt. %) preheated to 40° C. is added dropwise into olive oil at 40° C. under stirring at 420 rpm for 10 mM. Spontaneous gelation of the gelatin droplets is then driven by a 15° C. decrease in emulsion temperature followed by 30 mM of continued stirring. 100 ml of acetone is then added to the emulsion which is stirred for an additional 1 h. The resulting microspheres are then washed three times in acetone, recovered by centrifugation at 5000 rpm at 4° C. for 5 mM, and fractionated according to size through the use of sieves with different apertures. Following air-drying, the microspheres are crosslinked by placing them into an aqueous solution of glutaraldehyde and stirred at 4° C. for 15 h. Collection of the crosslinked microspheres is performed by centrifugation at 5000 rpm, for 5 mM at 4° C., and the crosslinking reaction is quenched by agitating the microspheres in 10 mM aqueous glycine solution at 37° C. for 1 h. Lastly, the microspheres are washed three times with double-distilled water and freeze dried in preparation for sterilization by ethylene oxide.

The advantage to using gelatin as a carrier for controlled release is that polyion complexation can be used to load the substance to be released into the matrix under mild conditions. If, for example, the protein to be released is present in the aqueous solution of gelatin during crosslinking, its effect will most likely be lost because of chemical deactivation. By simply preparing an aqueous solution of the protein and dropping it onto the freeze-dried gelatin carrier, allowing for sorption of the protein to the matrix and its subsequent sustained release in vivo through degradation of the carrier avoids this problem. In addition, this method provides a highly reproducible way of quantitatively loading charged biomolecules such as basic fibroblast growth factor into gelatin hydrogels regardless of their crosslinking extent, as long as the hydrogel mesh size is large enough to allow for inward diffusion of the biomolecules. Freeze-dried gelatin hydrogels are rehydrated with a solution of the substance of interest; however the volume used is much less than theoretically required to fully swell the crosslinked hydrogel.

Using sustained release compositions made of gelatin it is also possible to control the release rate by varying the extent by which the gelatin carrier is crosslinked. By varying the extent by which the gelatin carrier is crosslinked one can control hydrogel degradation, which in turn affects substance release since, for example the bound growth factor is only released into the surrounding environment still complexed with gelatin.

Substances to be released from the sustained release composition include substances which support growth or differentiation of the biological material. Such substances can include, but are not limited to cytokines, chemokines, nutrients supporting growth of biological material, such as cell nutrients, growth factors, growth hormone releasing hormone, granulocyte-colony stimulating factor, granulocyte macrophage-colony stimulating factor, macrophage-colony stimulating factor, interferon, insulin, atriopeptin-III, monoclonal/polyclonal antibody, TNF, macrophage activating factor, interleukin, tumor denaturing factor, urokinase and mixtures thereof. The sustained release compositions can also be loaded with drugs. The microfluidic continuous flow device can then be used for drug studies. Thus, to give an example the sustained release compositions can be loaded with drugs for chronicle disease studies.

Nutrients supporting growth of the biological material which can be loaded into the sustained release compositions can include for example non essential amino acids, salts (e.g. Ca and K), vitamins, lipids, glucose and mixtures thereof.

Examples of growth factors are those which belong to the following family of growth factors can include, but are not limited to the fibroblast growth factor family (FGF), the hedgehog family, the Wnt family, the TGF-β superfamily including the BMP family (classification derived from Developmental Biology, $6^{th}$ edition, Scott F. Gilbert, Sinauer Associates, Inc., Publisher, p. 149-153).

Individual examples of growth factors include, but are not limited to such as human growth hormone, bovine somatotropin, porcine somatotropin, insulin-like growth factor, epidermal growth factor, erythropoietin (EPO), bone morphogenetic protein, Epidermal growth factor (EGF), Hepatocyte growth factor (HGF), basic fibroblast growth factor (bFGF or FGF-2), Acidic fibroblast growth factor (aFGF or FGF-1), Myostatin (GDF-8), Granulocyte-colony stimulating factor (G-CSF), Transforming growth factor beta (TGF-β), Thrombopoietin (TPO), Platelet-derived growth factor (PDGF), Granulocyte-macrophage colony stimulating factor (GM-CSF), Growth differentiation factor-9 (GDF9), nerve growth factor (NGF), tissue plasminogen activator or neutrophins.

The sustained release compositions used herein can be of any desired shape. In one aspect the sustained release composition releasing at least one substance, which supports cultivation of the biological material, is present in a particulate form having dimensions which do not allow the sustained release composition to pass between the multiple through passages of the partitioning elements defining the compartment. In case the shape is not a result of the way the sustained release compositions have been manufactured, they can later on be formed in, for example, disk shape, cube shape, strips or spherical shape, such as a microsphere. In one example, a gelatin microsphere is used. The sustained release compositions can have a size range between about 5 μm to about 100 μm or between about 10 μm to about 50 μm.

It is also possible that the microfluidic continuous flow device comprises more than the above described one channel. Therefore, in one aspect the microfluidic continuous flow device of the present invention comprises multiple channels, such as 2, 4, 6, 8, 10, 12, 16 or even more. When combining several microfluidic continuous flow devices much higher numbers of channels can be obtained. Due to the fact that microfluidic devices use only very small amounts of liquid such devices can provide much more channels than a common culture well plate having for example 96, 384 or 1536 wells. Using multiple channels in one microfluidic continuous flow device different kinds of biological material can be cultivated in one device.

In still another aspect, the present invention refers to a microfluidic continuous flow device comprising:
    a first channel and a second channel each comprising a first and a second area, wherein the first area is a compartment which is defined by partitioning elements and the second area is a space arranged or located outside the compartment;
        wherein each of the channels has a first inlet for the compartment, a second inlet for introducing a cultivation medium into the space of the channel arranged outside of the compartment, and an outlet;
        wherein each of the second inlets and each of the outlets are arranged such as to allow a flow of cultivation medium through the channel; and
        wherein each of the second inlet of the first and second channel is in fluid communication with a common cultivation medium feeding line.

In another aspect the through passages which are formed between the partitioning elements are dimensioned such as to retain a biological material inside the compartment or the partitioning elements are dimensioned to allow supply of molecules into and out of the compartment by diffusion only. In still another aspect the compartment comprises a biological material.

An example of this specific aspect is illustrated in FIG. 15. Due to the fact that each of the second inlet 240 of the first and second channel is in fluid communication with a common cultivation medium feeding line 210 as illustrated in FIG. 15 it is possible to supply several channels with the same cultivation medium at the same time. It is also possible that this microfluidic continuous flow device comprises more than two channels, such as 2, 4, 6, 8, 10, 12, 16 or even more channels in one device.

In another aspect the microfluidic continuous flow device in which the cultivation medium inlets (second inlet) are connected to a common cultivation medium feeding line can also comprise at least one sustained release composition which is located together with the biological material in the compartment of each channel. This combination allows to culture different biological materials in different channels of the microfluidic continuous flow device but at the same time all channels are fed with the same cultivation medium. All substances specifically required by different biological materials can be supplied by sustained release compositions which release the substances which are specifically needed by the different biological materials in the different channels. Thus, the combination of sustained release compositions and several channels with different kinds of biological material allows cultivating multiple biological materials at the same time without the need of providing specific cultivation media for every biological material.

This can be illustrated by the following example. A microfluidic continuous flow device is used which comprises two channels, wherein the cultivation medium inlets of these two channels are connected to a common cultivation medium feeding line through which a 1:1 mixture of DMEM:F12K is fed as cultivation medium into both channels (see for example the two channel configuration in FIG. 15 or FIG. 20B). In this example, the compartment of the first channel comprises A549 cells and a sustained release composition releasing transforming growth factor α. The compartment of the second channel comprises HK-2 cells and a sustained release composition releasing epidermal growth factor (EGF). Transforming growth factor α can promote A549 growth but would inhibit HK-2 growth. On the other hand, the epidermal growth factor (EGF) can promote HK-2 growth but would inhibit A549 growth. In the exemplary configuration mentioned above only one type of medium needs to be supplied to the device but two cell types can be grown in different channels even though both cell types have different requirements as to the supplement needed for their growth.

All previous comments with respect to the microfluidic continuous flow device described at first also apply to this embodiment.

In another aspect, the present invention refers to a microfluidic continuous flow device comprising:
a first channel and a second channel each comprising a first and a second area, wherein the first area is a compartment which is defined by partitioning elements and the second area is a space outside the compartment;
wherein each of the channels has a first inlet into the compartment, a second inlet for introducing a cultivation medium into the space of the channel arranged outside of the compartment, and an outlet;
wherein each of the second inlets and each of the outlets are arranged such as to allow a flow of cultivation medium through the channel; and
wherein the first and the second channel are fluidly connected to each other wherein the outlet of the first channel is fluidly connected to the second inlet of the second channel.

In another aspect the through passages which are formed between the partitioning elements are dimensioned such as to retain a biological material inside the compartment or the partitioning elements are dimensioned to allow supply of molecules into and out of the compartment by diffusion only. In still another aspect the compartment comprises a biological material.

This specific example can be used to simulate the sequence of different tissues within a living organism. Due to the fact that the cultivation medium inlet of the second channel is not connected with a cultivation medium feeding line but is fluidly connected with the outlet of the first channel all metabolic products from the biological material in the first channel which have been transferred out of the compartment in the stream of cultivation medium are introduced into the second channel. This specific set up of a microfluidic continuous flow device resembles the natural order in a living organism in which the body fluid, such as blood, flows from one tissue or organ to another one.

In another aspect, the microfluidic continuous flow device comprises multiple channels, wherein each channel is fluidly connected with a subsequent channel, wherein the fluid connection is established between the outlet of a preceding channel and the second inlet of the subsequent channel. In this example, multiple channels of a microfluidic continuous flow device are connected in series to resemble the flow of a medium in a living organism.

In still another example, the microfluidic continuous flow device comprises multiple channels, wherein the outlet of the first channel is fluidly connected with the second inlet of the subsequent channels. Sometimes it is required to supply different biological materials with a substance coming from a previous channel to allow proper cultivation. In this case all subsequent channels are fluidly connected to the outlet of this first channel. As shown exemplarily in FIG. 18, the outlet of a first channel comprising lung cells (such as A549) is fluidly connected to three other channels which comprise liver (such as HepG2/C3A), kidney (such as HK-2) and fat cells (such as primary human adipocytes). The rationale for the choice of these four organs is that lung, liver and kidney are the three vital organs with drug metabolic activities (Sheweita, S. A., 2000, Current Drug Metabolism, vol. 1, p. 107). Fat is considered an endocrine organ which actively regulates body weight homeostasis and energy balance (Schaffler, A., Muller-Ladner, U., et al., 2006, Endocrine Reviews, vol. 27, no. 5, p. 449).

Although the cells are perfused by the same cultivation medium, they still experience their specific soluble microenvironments. Such a microfluidic continuous flow device can be used, for example as an in vitro model for drug testing. For example, naphthalene can be introduced into the multi-channel system as an illustrative proof-of-concept study showing that, the cells cultured in different channels can still communicate with each other, and will therefore response collectively to a drug.

It should be noted that it is also possible to culture different biological materials in one compartment of one channel in order to simulate for example the structure in an organ of an organism. As mentioned before culturing different biological materials within one channel can either be achieved by introducing them one by one or by coating the surface of the compartment with capture molecules which bind to different parts of different biological materials.

All previous comments with respect to the microfluidic continuous flow device described at first also apply to this embodiment.

In still another aspect the present invention refers to a method of cultivating biological material in a microfluidic continuous flow device, wherein the method comprises:
providing the microfluidic continuous flow device having a channel;
wherein the channel comprises a first and a second area wherein the first area is a compartment which is defined by partitioning elements and the second area is a space outside the compartment;
wherein through passages which are formed between the partitioning elements are dimensioned such as to retain a biological material and a sustained release composition inside the compartment;
wherein the channel has a first inlet for introducing biological material into the compartment, a second inlet for introducing cultivation medium into a space of the channel arranged outside of the compartment, and an outlet;
wherein the second inlet and the outlet are arranged such as to allow a flow of cultivation medium through the channel;
introducing a biological material and a sustained release composition into the compartment via the first inlet;
wherein the sustained release composition releases at least one substance which supports cultivation of the biological material and which is not initially comprised in the cultivation medium; and
transporting a cultivation medium for cultivation of the biological material through the channel via the second inlet.

In one aspect the through passages which are formed between the partitioning elements are dimensioned such as to allow supply of molecules into and out of said compartment by diffusion.

In another aspect, the present invention refers to a method of cultivating biological material in a microfluidic continuous flow device, wherein the method comprises:
providing the microfluidic continuous flow device having a first and a second channel;
wherein each channel comprises a first and second area wherein the first area is a compartment which is defined by partitioning elements and the second area is a space outside the compartment;
wherein through passages which are formed between the partitioning elements are dimensioned such as to retain a biological material inside the compartment;
wherein each channel has a first inlet for introducing biological material into the compartment, a second inlet for introducing cultivation medium into a space of the channel arranged outside of the compartment, and an outlet;
wherein each of the second inlets and each of the outlets are arranged such as to allow a flow of cultivation medium through the channel;
wherein each of the second inlets of the first and second channel is in fluid communication with a common cultivation medium feeding line;
introducing biological material into each of the compartments via each of the respective first inlets; and
transporting a cultivation medium via the common cultivation medium feeding line through each of the two channels.

In one aspect the through passages which are formed between the partitioning elements are dimensioned such as to allow supply of molecules into and out of said compartment by diffusion. In another aspect the method also comprises introducing at least one sustained release composition into one or each of the compartments.

In another aspect the present invention refers to a method of cultivating biological material in a microfluidic continuous flow device, wherein the method comprises:
providing the microfluidic continuous flow device having a first and a second channel;
wherein each channel comprises a first and a second area wherein the first area is a compartment which is defined by partitioning elements and the second area is a space outside the compartment;
wherein through passages which are formed between the partitioning elements are dimensioned such as to retain a biological material inside the compartment;
wherein each channel has a first inlet for introducing biological material into the compartment, a second inlet for introducing cultivation medium into a space of the channel arranged outside of the compartment, and an outlet;
wherein each of the second inlets and each of the outlets are arranged such as to allow a flow of cultivation medium through each of the channels;
wherein the first and the second channel are fluidly connected to each other wherein the outlet of the first channel is fluidly connected with the second inlet of the second channel;
introducing biological material into each of the compartments via each of the respective first inlets; and
transporting a cultivation medium through the first and second channel by introducing a cultivation medium into the first channel via the second inlet of the first channel.

In one aspect the through passages which are formed between the partitioning elements are dimensioned such as to allow supply of molecules into and out of said compartment by diffusion. In another aspect the method also comprises introducing at least one sustained release composition into one or each of the compartments.

The flow rate of the cultivation medium through the space in the channel lying outside the compartment depends on the biological material cultured within the compartment. In one aspect of the present invention the cultivation medium flows through each channel comprised in the microfluidic continuous flow device at a flow rate between about 30 μl/h to about 220 μl/h. In some examples it is also possible that the flow rate in different channels is different. Different flow rates could be usable when culturing different biological materials in different channels.

In another aspect the method further comprises introducing a test substance into the cultivation medium. By introducing one or two or even more test substances into the cultivation medium the reaction of the biological material located in the cells to this substance can be examined. Such a substance can be a compound or composition which is or which is suspected to be teratogenic, cancerogenic, mutagenic, psychogenic or toxic, and mixtures thereof. Such a substance can also be a substance which is suspected to be of importance for growth or differentiation of the biological material located in the compartment. This allows improving the culture conditions for different biological materials located in different or the same compartment.

In still another aspect the present invention refers to a kit comprising a microfluidic continuous flow device of the present invention. Those kits can further include a biological material or at least one sustained release composition comprised in the compartment(s) of the microfluidic continuous flow device of the present invention or both, a biological material or at least one sustained release composition. Furthermore, such kits can also comprise at least one cultivation medium which is suitable for cultivation of the biological material comprised.

The above described microfluidic continuous flow devices, methods and kits can be used for carrying out cell migration studies or gene expression analysis, or cellular function and differentiation studies, or disease diagnosis, or drug or toxicity testing. The devices can also be used as an early drug screening tool in the development of new drugs. In this case putative drugs are fed into the channel and the reaction of the biological material inside the compartment is tested. Those drugs can be added to the cultivation medium or can be loaded into sustained release compositions.

By "consisting of" is meant including, and limited to, whatever follows the phrase "consisting of". Thus, the phrase "consisting of" indicates that the listed elements are required or mandatory, and that no other elements may be present.

By "comprising" it is meant including, but not limited to, whatever follows the word "comprising". Thus, use of the term "comprising" indicates that the listed elements are required or mandatory, but that other elements are optional and may or may not be present.

The inventions illustratively described herein may suitably be practiced in the absence of any element or elements, limitation or limitations, not specifically disclosed herein. Thus, for example, the terms "comprising", "including", "containing", etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the inventions embodied therein herein disclosed may be resorted to by those skilled in the art, and that such modifications and variations are considered to be within the scope of this invention.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

Other embodiments are within the following claims and non-limiting examples. In addition, where features or aspects of the invention are described in terms of Markush groups, those skilled in the art will recognize that the invention is also thereby described in terms of any individual member or subgroup of members of the Markush group.

EXPERIMENTAL SECTION

Manufacture of a Microfluidic Flow Device

Microfluidic channels with micropillar arrays were designed using AutoCAD (Autodesk, USA). The dimensions of the microfluidic channel were 1 cm (length)×600 μm (width)×100 μm (height); and each microfluidic channel has an inlet for supplying biological material into the compartment, one inlet for supplying medium into the space outside the compartment and one outlet. An array of 30×50 μm elliptical micropillars with a 20 μm gap size is situated in the center of the microfluidic channel, bounding a cell residence compartment that is 200 μm wide. Silicon templates were fabricated by standard deep reactive ion etching (DRIE) process (Alcatel, France). The microfluidic channels were then obtained by replica molding poly(-dimethylsiloxane) (PDMS) (Sylgard 184, Dow Corning, USA) on the silicon templates. For this, the mixture of curing agent and prepolymer PDMS is poured over the silicon template and cured at 65° C. overnight before peeling off. The ratio is 1:10 (curing agent: PDMS). The solidified PDMS structures were plasma-oxidized in oxygen plasma for 1 min (125 W, 13.5 MHz, 50 sccm, and 5.33 Pa or 40 millitorr for irreversible bonding to glass coverslips before connecting to fluidic components (Upchurch, USA). The first inlet through which biological material, such as cells and microspheres is introduced into the compartment of the microfluidic channel was connected to a cell reservoir, which comprised of a two-way valve with a luer connection (Cole-Palmer, USA) coupled to a 22G stainless steel hypodermic needle (Becton-Dickinson, USA). The other inlet and outlet are for cell cultivation medium perfusion. The entire set-up was sterilized by autoclaving at 105° C. for 30 min.

Fabrication of Pneumatic PDMS Valve

Pneumatic PDMS valves and their manufacture are known in the art as described for example by Unger, M. A., Chou, H.-P (2000, Science, vol. 288, p. 113). The technical design of a PDMS valve as illustrated in FIGS. 22 A and B is drawn according to the pattern illustrated in FIG. 22 C with AutoCAD®. In FIG. 22 the horizontal line 610 shows the channel while 620 shows the position of the pneumatic valve. For manufacturing via soft lithography the AutoCAD® drawing shown in FIG. 22 C is translated into the master, which is a silicon template coated with SU8 2010 photoresist. A 1:20 PDMS mixture (1 part curing agent, 20 parts PDMS) is spin-coated on to the silicon template at 1500 rpm for 30 seconds, forming a 15 μm layer. After being baked at 65° C. for 20 minutes, the thin layer of PDMS valves is peeled off and can be aligned with the layer of microfluidic channel to create a system of 2 layers of PDMS. After alignment, the two PDMS layers are kept at 65° C. for at least 4 hours and brought together. The valve can be positioned on top of the channel of the microfluidic continuous flow device directly before the or after the second inlet or the first inlet. The dimensions of the valve depend on the dimension of the microfluidic continuous flow device. In one example the dimensions are about 200× 200 μm.

Setting Up of an Operational Control System Including the Microfluidic Flow Device The pneumatic valves are directly controlled by pressured gas. Thus, to precisely control the pressured gas which is the driving force of the pneumatic valves, an operational control system is set up. FIG. 16 illustrates the set-up of an exemplary operational control system. The gas tank 410 is connected by plastic tubings to a pressure regulator 430 which has a digital meter. By adjusting the meter, the pressure of gas is controlled that goes through the pressure regulator 430. The pressure regulator 430 is then connected to the chip 420 via the solenoid valve 440 that works as an electrical switch which is electronically activated. If they are switched on, gas can go through the solenoid valves 440 and cause deformation of the pneumatic valves in the microfluidic device 420. The solenoid valves are controlled by computer 450 through a 24 volt electric output 460.

Operational Perfusion System Including the Microfluidic Flow Device

FIG. 17 illustrates the schematic set up of a perfusion system including the microfluidic flow device. At first, cells are withdrawn from a cell reservoir (not shown in FIG. 17) into the channels of the microfluidic flow device 530 by two withdrawal pumps 510 at the outlet. FIG. 17A is the schematic representation. During perfusion cultivation medium keeps circulating, see FIG. 17B. The cultivation medium is withdrawn from a cultivation medium storage tank 560 via a peristaltic pump 580. Oxygen permeable tubing 570 ensures that the oxygen level in the cultivation medium is sufficient for survival of the cells in the channel of the microfluidic device. After passing a regulative four way valve 520 and a bubble trap 550 the cultivation medium is perfused through the channel of the microfluidic device. As can be seen from FIG. 17, cultivation medium from the two channels is sufficiently mixed before being infused into the channels again. Thus, the two channels are fluidically linked.

Introducing Cellular Aggregates into the Microfluidic Channel

Cells can be introduced into the compartment of the microfluidic flow device in a mixture of single cells or as cell aggregates. Cell aggregates tend to fill up the compartment of the channel faster than single cells as the cell aggregates are stopped more effectively by the pillars and as the aggregates are larger than single cells. In one example such 3D cellular aggregates are pre-induced before introducing the cells into the compartment of the microfluidic flow device. In order to induce 3D cellular aggregates, the cell surface can be modified to generate reactive target sites for ligation. In this example a chemical modification of the cell surface is carried out. Therefore, a transient polymeric inter-cellular linker with multiple hydrazide handles on a polyethylenimine (PEI) backbone has been synthesized and characterized to react with aldehyde functional groups on cell surfaces, modified by sodium periodate, to induce cellular aggregation (FIG. 19) (Ong, S. M., He, L., et al., 2007, Biomaterials, vol. 28, no. 25, p. 3656). This product is referred to as PEI-hydrazide, PEI-hy. Being a polymer of low molecular weight (MW~2000 KDa), The PEI-hy does not pose mass transport difficulties that bulk biomaterials like hydrogels and scaffolds do.

To synthesize PEI-hy, thiol groups were first conjugated onto PEI (MW 1800) by reacting with 2-iminothiolane. Twenty milligrams of PEI (MW 1800) was added to 15 mg of 2-iminothiolane in 2 ml of distilled water and reacted for 2 h at room temperature. 25.6 mg of E-maleimidocaproic acid hydrazide (EMCH Pierce, USA) in 1 ml PBS was added and reacted for 4 h at room temperature. EMCH contains maleimide groups and hydrazide groups. The maleimide group reacts with the thiol groups to form a thioether linkage, yielding PEI molecules with conjugated hydrazide groups. The final product was isolated by eluting through a PD-10 column (Amersham Pharmacia Biotech AB, Piscataway, USA) with distilled water and freeze-dried.

To modify the cells, single cells were re-suspended in cold sodium periodate or PBS (control) and incubated at 4° C. in the dark for 15 min. Cold PEI-hy or neutral hydrazide or PBS (control) was then added and incubated with the cells for 30 min at 4° C. on an orbitron shaker (Model 260200, Boekel Scientific, US). For 7-day culture, the aggregates formed were washed with PBS and re-suspended in cultivation medium; placed on an orbital shaker (Spectra-teknik, USA) rotating at 50 rpm at 37° C. in a humidified environment with 5% $CO_2$.

Examples for other multivalent inter-cellular linkers are dendrimer hydrazides. For example, multivalent inter-cellular linkers were hydrazide derivatives of ethylenediamine, DAB-AM-4, DAB-AM-8, and DAB-AM-16, synthesized in a 2-step reaction. Firstly, the primary amines were reacted with methyl acrylate to yield the intermediate esters of ethylenediamine ester, DAB-AM-4 ester, DAB-AM-8 ester, and DAB-AM-16 ester. They were verified by the appearance of a methyl ester peak at $\delta=\sim3.62$ ppm in the $^1$H NMR spectra and wave number=~743 $cm^{-1}$ in the FT-IR (Fourier transform infrared) spectra. $^1$H NMR spectra demonstrated the successful synthesis of 4, 8, 16 and 32 arms intermediate esters, further confirmed by mass spectrometry. In the second step, all the methyl esters were treated with hydrazine monohydrate to yield the final hydrazide derivatives of ethylenediamine hydrazides, DAB-AM-4 hydrazides, DAB-AM-8 hydrazides, and DAB-AM-16 hydrazides. The hydrazide derivatives were verified by a hydrazide hydrogen peak at $\delta=\sim9.00$ ppm in the $^1$H NMR spectra and wave number=~1650 $cm^{-1}$ in the FT-IR spectra. $^1$H NMR spectra demonstrated the successful synthesis of 4, 8, 16 and 32 arms hydrazide, further confirmed by mass spectrometry. Therefore, hydrazide derivatives of ethylenediamine, DAB-AM-4, DAB-AM-8, and DAB-AM-16 with 4, 8, 16 and 32 arms hydrazide, respectively, as multivalent inter-cellular linkers were synthesized (Zhao, D., Ong, S.-M., Dendrimer hydrazides as multivalent transient inter-cellular linkers, Biomaterials, epub 12 Jun. 2008).

As for PEI-hydrazide, cells are first modified with sodium periodate ($NaIO_4$) to create aldehyde groups on their surface before they are reacted with dendrimer hydrazides.

Introduction of A549, HK-2 and HepG2/C3A Cells and Investigation of Cell Viability in the Compartment of the Microfluidic Flow Device At first the compartment of the channel of the microfluidic flow device is seeded with cells. Cells which have been used for seeding and the following viability tests are lung cells (carcinomic human alveolar basal epithelial cells), proximal tubular human kidney cells and the human hepatocellular carcinoma cell line HepG2/C3A (liver).

All cell culture components are purchased from GIBCO, Invitrogen, USA unless otherwise stated. A549 cells (ATCC, USA) were cultured in F12K supplemented with 10% fetal calf serum, 1.5 g/l sodium bicarbonate, 2 mM L-glutamine, 100 units/ml penicillin and 100 g/ml streptomycin. C3A cells (ATCC, USA) were cultured in Minimum Essential Medium supplemented with 10% fetal calf serum, 1.5 g/l sodium bicarbonate, 1 mM sodium pyruvate, 100 units/ml penicillin and 100 g/ml streptomycin. HK/2 cells (ATCC, USA) were cultured in F12K supplemented with 10% fetal bovine serum, 1.5 g/l sodium bicarbonate, 100 units/ml penicillin and 100 g/ml streptomycin.

Cell aggregates have been chemically modified with PEI-hy using the above protocol. For seeding small cell aggregates pre-formed under the condition listed in Table 1 the cells are withdrawn into the microfluidic channel at a flow rate of 30 μl/h. During the seeding process, small cell aggregates merge into one another and form bigger aggregates as they move along in the compartment of the channel. A schematic snapshot of this seeding process is shown in FIG. 8. Upon finishing seeding, cultivation medium is infused into the channel at a flow rate of 40 μl/h for 20 minutes to remove any displaced cells which have been seeded in the space of the channel outside the compartment. The entrapped cells are finally left for perfusion culture at a flow rate of 30 μl/h for three days.

TABLE 1

| Conditions for modification of cells prior to seeding | | |
| --- | --- | --- |
| | Sodium Periodate | PEI-hydrazide |
| Concentration | 0.5 mM | 0.006 mM |
| Incubation time | 13 minutes | 0 minutes |
| Incubation temperature | 4° C. | Room temperature |

To investigate the viability of the cells after three days of perfusion culture, live cells are stained green by 20 μM Calcein AM (Molecular Probes, USA), and dead cell are stained red by 50 μg/ml Propidium iodide (PI). The fluorescent dyes are perfused through the microfluidic channel at a flow rate of 0.4 ml/h for 30 minutes followed by cultivation medium for 10 minutes to remove all dyes. This high flow rate is used for the purpose of fluorescence staining of the cells. Cells are visualized under confocal microscope (Olympus Fluoview 500, Japan) and the viability images of A549, HepG2/C3A, and HK-2 are shown in FIG. 11. As can be seen from FIG. 11, first row of pictures the number of dead cells (encircled) is very low compared to the living cells which shows that cells are able to survive and grow in the microfluidic flow device.

To observe the 3D morphology of the cells in the microfluidic channel after perfusion culture, the cells are fluorescently labeled with TRITC-phalloidin (Molecular Probes, USA) for assessment of F-actin distribution using confocal microscope. As can be seen in FIG. 12 the morphology of these A549 and HepG2/C3A cells is similar to the natural (in vivo) three dimensional morphology of the cells in tissue when compared to two dimensional monolayers which can be observed in culture flasks.

Fabrication of Sustained Release Formulations

Cells can be seeded into the compartment of the microfluidic flow device together with sustained release formulations. Manufacturing of sustained release formulations is illustrated in the following on the basis of gelatin microspheres. Gelatin microspheres were fabricated via glutaraldehyde crosslinking of a gelatin aqueous solution in a water-in-oil emulsion technique. To create the water-in-oil emulsion, 4 g aqueous solution of gelatin (10 wt. %) preheated to 37° C. was added dropwise into 300 ml olive oil (Bertolli, Italy) under continuous stirring at 1250 rpm for 10 minutes. Spontaneous gelation of the gelatin droplets was then driven by a 15° C. decrease in emulsion temperature followed by 24 hours of agitation at top speed. The resulting microspheres were then washed three times in acetone, recovered by centrifugation at 5000 rpm at 4° C. for 8 minutes. The crosslinking reaction was then quenched by agitating the microspheres in 100 mM aqueous glycine solution for 1 hour. Lastly, the microspheres were washed three times with distilled water and freeze dried. The morphology of the microspheres was observed under light-transmitted microscopy (FIG. 3B, left picture), and phase contrast images (FIG. 3B, right picture) were taken to evaluate their sizes. As shown in FIG. 3B the diameters of the microspheres fall within the range of 20 to 50 μm.

Loading of Sustained Release Compositions with Substances

The sustained release compositions such as the gelatin microspheres are loaded by letting them soak up the substance or combination of substances to be released later on from the sustained release composition. For example, for loading a gelatin microsphere with TGF-β1 the following protocol can be used.

3 mg of gelatin microspheres as prepared above was soaked in 0.5 ml of 500 ng/ml TGF-β1 solution, and the mixture was incubated overnight at 4° C. for TGF-β1 loading. The mixture was centrifuged at 5000 rpm for 8 minutes, followed by supernatant collection everyday.

Characterization of Gelatin Microspheres

To test the continuous release of TGF-β1 2% BSA solution was topped-up to the gelatin microspheres. TGF-β1 was released from gelatin microspheres at 37° C. The accumulative amount of released TGF-β1 from the gelatin microspheres was measured by an ELISA kit (Promega, USA) (FIG. 21).

In another experiment gelatin microspheres were loaded with FITC-dextran (Sigma, USA) with molecular weight of 70 KDa and 150 KDa. 10 μg of FITC-dextran was loaded into 1.6 mg of gelatin microspheres; the mixture is then topped-up with 1×PBS to 100 μl and kept at 4° C., overnight, for molecule loading. On the next day, the suspension was centrifuged at 5000 rpm for 8 minutes, and the supernatant was collected for quantification of unloaded molecule by a microplate reader (TECAN, Switzerland). After the supernatant was collected, the suspension is topped-up with 1×PBS to 100 μl again for the continuous molecule release over time. This procedure is repeated for the following six days. Therefore, it was possible to evaluate the control release properties of the gelatin microspheres as shown in FIG. 6. Y-axis is the accumulative amount of FITC-dextran over 5 days. On a daily basis, the amount of released molecule remains constant, which is indicative of the control release behavior of the gelatin microspheres that were fabricated.

Entrapment of Gelatin Microspheres in the Microfluidic Channel

The gelatin microspheres are to be incorporated into the compartment of the 3D microfluidic channel to create soluble microenvironments. This is based on the hypothesis that the molecules released from the gelatin microspheres could remain in the compartment of the microfluidic channel, defined by the micro-pillar array, rather than being removed by perfusion. In order to validate this hypothesis, gelatin microspheres (loaded with FITC-dextran) were seeded into the compartment of the microfluidic channel and perfuse the system with 1×PBS to mimic the fluidic environment. The PBS that flows out (1 ml everyday) from the microfluidic channel were collected to quantify the fluorescence intensity, which could reflect the amount of released molecules that is removed from the microfluidic channel.

Furthermore, at the end of this perfusion experiment, the number of gelatin microspheres in the compartment of the channel was quantified by confocal microscopy (Zeiss, Germany). According to this quantification, the exact same amount of gelatin microspheres (loaded with FITC-dextran) to quantify the amount of released FITC-dextran in static conditions was measured. In static conditions, the same amount of microspheres were kept in 1 ml 1×PBS to allow molecule release. On a daily basis, the microspheres were centrifuged at 5000 rpm for 5 minutes, and the supernatant (FITC-dextran contained PBS) was collected for further fluorescence intensity measurement. After this step, 1 ml of fresh PBS is topped-up to the microspheres for molecule release. This was repeated on a daily basis. This experiment was set as a static control. Since the accumulative amount of released FITC-dextran in perfusion was less than that in static (see FIG. 7), it can be concluded that released FITC-dextran remains in the compartment of the microfluidic channel. This proves that a soluble microenvironment can be created.

FIG. 2A shows the process of seeding gelatin microspheres into the compartment of the microfluidic channel together with cells as well as the packing of gelatin microspheres and cell mixture in the microfluidic channel. The cells are fixed and stained with Propidium iodide (PI) (Molecular Probes, USA). The pictures are taken at different sites of one microfluidic channel by a confocal microscope (Olympus Fluoview, Japan). From the pictures, it can be concluded that the gelatin microspheres can get evenly distributed along the microfluidic channel. An even distribution of the gelatin microspheres in the compartment of the microfluidic channel provides for a uniform concentration gradient of the released compounds or compositions from the sustained release components in the whole compartment of the microfluidic channel. Thus, even distribution of the sustained release formulations, such as gelatin microspheres can effectively minimize the concentration gradient.

Characterizing and Controlling the Soluble Microenvironment in the Compartment of the Microfluidic Channel The ratio of cell number to the number of the gelatin microspheres, as well as the cross-linking density of the gelatin microspheres can be manipulated to control the soluble microenvironment in the compartment of the microfluidic flow device. By adjusting the ratio of cell number to gelatin microspheres, or the cross-linking density of the gelatin microspheres, the concentration of the growth factors released from the gelatin microsphere carriers into the microenvironment can be controlled. The following table indicates the ratios and cross-linking densities which were investigated.

TABLE 2 the cell/bead ratios and cross-linking densities

| Cell/bead ratio | Cross-linking density |
|---|---|
| 20 | 25% Glutaraldehyde |
| 40 | 15% Glutaraldehyde |
| 100 | 10% Glutaraldehyde |
| 200 | 5% Glutaraldehyde |

FITC-dextran was used again as the probe to visualize the microenvironment. They were loaded into the gelatin microspheres and introduced into the microfluidic channel together with cell suspension. The concentration of the soluble microenvironment at cell vicinity was closely correlated with the average fluorescence intensity that can be detected. As shown in FIG. 13 (c, d), the X axis represents the distance across the microfluidic channel. Thus, the image along the X axis was scanned, in a layer-by-layer manner, with an increment of 5 μm. The average fluorescence intensity on each layer can be calculated by Image-Pro® Plus (Media Cybernatics Inc., Md.). Finally, at a certain cross-linking density, or a certain cell/gelatin microsphere ratio, the fluorescence intensity of the microenvironment in the microfluidic channel was obtained. The relation is represented in FIG. 14. If the cell/gelatin microsphere ratio increases, the fluorescence intensity increases accordingly. And if the cross-linking density increases, the fluorescence intensity decreases.

Microfluidic Continuous Flow Device for Culturing Different Cell Types

In this section, an application is described in which a soluble microenvironment for exemplary cell types was created. Four different cell types were cultured in four different channels wherein the first and second channel were connected in a series with each other, i.e. the outlet of the first channel is in fluid communication with the inlet for the medium of the second channel. Cell lines HepG2/C3A, A549, HK-2 and primary human adipocytes were chosen to mimic lung, liver, kidney and fat. The rationale for the choice of these four organs is that lung, liver and kidney are the three vital organs with drug metabolic activities (Sheweita, S. A., 2000, Current Drug Metabolism, vol. 1, p. 107). Fat is considered an endocrine organ which actively regulates body weight homeostasis and energy balance (Schaffler, A., Muller-Ladner, U., et al., 2006, Endocrine Reviews, vol. 27, no. 5, p. 449).

Although the cells were perfused by the same basal medium, they still experience their specific soluble microenvironments. This multi-channel system included an operational control system based on the software of Labview®. Naphthalene was introduced into the multi-channel system for a proof-of-concept study that the cells cultured in different channels can still communicate with each other and response collectively to, e.g., a drug in case they are used for testing drugs and their effects on the four different cell types.

A microfluidic continuous flow device with a four-channel system is shown in FIG. 18. The system has one second inlet 710 and four outlets 730 which are connected to external valves (not shown). The first channel is connected via the line 740 with the second inlet of the other three channels. During perfusion culture, the outlet at the first "lung" channel is closed, so that cultivation medium will perfuse the lung cells first and flow in parallel into the other three channels (liver, kidney, fat). This flow profile is the same as physiological circulatory that blood comes from the lung and get distributed in the other organs. Each channel has an individual first inlet 720 (indicated by black arrows) for supplying cells into the compartment of the microfluidic continuous flow device.

The functions of the cell lines which were chosen to investigate are closely related to the metabolism of drugs. (Table 3) Most of the drugs were metabolized by the cytochrome P450 pathways. Ethoxyresorufin is deethylated by Cytochrome P450 3A4 (CYP3A4) and CYP1A2 in adult human liver. Both CYP3A4 and CYP1A2 are the enzymes involved in phase I metabolism. UGT is an enzyme involved in phase II metabolism. GGT, the function of which is involved in detoxification, is unique in the kidney. However, adipose tissue does not exhibit specific metabolic function. When the adipocytes are cultured in the 3D microfluidic channel, the medium that is perfused out from the channel was collected daily. The concentration of the secreted adiponectin in the collected medium is determined by the adiponectin ELISA kit.

TABLE 3 cell functions to be investigated

| Cells | Functions |
|---|---|
| Lung (A549) | Ethoxyresorufin O-deethylase (EROD) activity |
| Kidney (HK-2) | Gamma-Glutamyl transpeptidase (GGT) activity |
| Liver (HepG2/C3A) | UDP-Glucuronyl transferase (UGT) activity |
| | Ethoxyresorufin O-deethylase (EROD) activity |
| Primary adipocytes | Adiponectin secretion |

7-Ethoxyresorufin-O-Deethylation (EROD) Assay

The deethylation of ethoxyresorufin is CYP 1A associated and its activity were quantified under a confocal microscope according to Chia et al., (2000, Tissue Engineering, vol. 6, p. 481). Briefly, 7-ethoxyresorufin is perfused through the cell column in the microfluidic channel at 30 μl/hr for 4 hours followed by visualization of the microfluidic channel under a confocal microscope (Olympus Fluoview 500) with a rhodamine filter. The images were then processed with Image-Pro® Plus (Media Cybernatics Inc., Md.) to quantify the EROD activity in terms of fluorescence intensity per cell.

UDP-Glucuronosyltransferase (UGT) Assay

The enzyme has the ability to metabolize the substrate 4-methylumbelliferone (MU) into 4-methylumbelliferone-glucuronide (MUG). Thus, the enzyme activity is indicated by the amount of 4-MUG produced by the cells.

Capillary electrophoresis (CE) with fluorimetric detection was used for the simultaneous detection of 4-MU and 4-MUG. Separation is carried out on an untreated fused silica capillary with fluorimetric detection using an excitation wavelength of 320 nm with a 375 nm cut off emission filter. Different concentrations of 4-MU dissolved in Krebs-Hanseleit buffer (Hiller, D. L. and Cole, R. O., 1995, Anal. Biochem., vol. 227, p. 251) were perfused through the microfluidic channel at 30 μl/h to calculate the Michaelis-Menten kinetics. Aliquots of the supernatant medium were withdrawn at different time points to investigate the enzymes time dependence for analysis. 4-MU standards were prepared from a 0.1 mg/ml stock solution in 0.1 M sodium phosphate buffer (pH 6.5). 4-MUG standards were prepared from a 1 mg/ml stock in 0.1 M sodium phosphate buffer (pH 6.5). All standards were diluted with Krebs-Hanseleit buffer.

Gamma-Glutamyl Tranpeptidase (GGT) Activity Assay

This enzyme can metabolize its substrate γ-glutamyl-p-nitroanilide into p-nitroanilide. Thus, the enzyme activity is indicated by the amount of p-nitroanilide produced by the cells.

The product of p-nitroanilide is fluorescent. Therefore, the microplate reader (TECAN, Switzerland) was used to correlate the fluorescence intensity of p-nitroanilide with its concentration. The excitation/emission wavelength of p-nitroanilide is 410 nm/465 nm. Different concentrations of γ-glutamyl-p-nitroanilide (Sigma, USA) were perfused through the microfluidic channel seeded with HK-2 cells at 0.5 ml/h for 30 to 60 minutes. This is to allow for the complete reaction of the enzyme with the substrate. Medium perfused out from the microfluidic channel was collected for detection of fluorescence intensity. The standards of γ-glutamyl-p-nitroanilide and p-nitroanilide (Sigma, USA) were prepared from a 2 mM stock solution in 0.1 M, pH 8 Tris-HCl buffer.

Introduction of BMSC Cells and Investigation of Cell Viability in the Compartment of the Microfluidic Flow Device In another experiment formation of cell aggregates of bone marrow mesenchymal stem cells (BMSC) and seeding them in the compartment of the microfluidic continuous flow device is demonstrated. Additional viability test demonstrate the suitability of the device of the present invention for this application.

Cell culture components were purchased from GIBCO, Invitrogen, USA unless otherwise stated. Bone marrow mesenchymal stem cells were harvested from the bone marrow of male Wistar rats and cultured in low glucose Dulbecco's Modified Eagle's Medium supplemented with 10% fetal calf serum and 1.5 g/l sodium bicarbonate. Osteogenic medium was prepared by supplementing basal medium with 100 nM dexamethasone, 50 mM ascorbic acid 2-phosphate and 10 mM b-glycerophosphate (Merck, Singapore).

Cells were first modified with 0.5 mM of sodium periodate (NaIO4) (Sigma) in test tubes at 4° C. in the dark. Cell seeding was performed by withdrawing a suspension (50 ml) of modified cells (6 million/ml) and dissolved inter-cellular linker (6 mM PEI-hy) from the cell reservoir, via the outlet using a withdrawal syringe pump at a flow rate of 30 μl/h. Upon filling up of central cell compartment, the cell reservoir was closed and cultivation medium infused from the inlet at a flow rate of 30 μl/h.

The cells were cultured in a one-pass perfusion manner with a syringe pump (Cole-Palmer) at 30 μl/h. The microfluidic system was placed onto a heating plate (MEDAX GmbH & Co. KG, Germany) maintained at 37° C. throughout the culture period in a sterile hood. Sixty millimolar of Hepes buffer (GIBCO, Invitrogen, USA) was added to the cultivation medium to maintain its pH at 7.4-7.6.

Cell viability of BMSCs after 3 days of perfusion culture in the gel free compartment of a microfluidic continuous flow device was assessed by perfusing 5 mM of calcein AM (Molecular Probes, USA) and 25 mg/ml of propidium iodide at 0.5 ml/h for 30 mM and viewing immediately by confocal microscopy (Fluoview 300, Olympus, Japan).

F-actin distribution in BMSCs was assessed after 3 days of perfusion culture in the gel-free microfluidic continuous flow device. In situ F-actin staining was performed after fixation with 3.7% paraformaldehyde (PFA) (30 min) by infusing the microfluidic channel via the second inlet with 0.5% Triton-X 100 (USB Corp, USA) (30 min), 0.2% bovine serum albumin (BSA) (30 min), 0.2 mg/ml of TRITC-phalloidin (Invitrogen, Singapore) (20 min) and 1×PBS (15 mM) at 0.5 ml/h. 2D monolayer cultures were fixed with 3.7% PFA (15 min) and stained by incubating with 0.5% Triton-X 100 (10 min), 0.2% BSA (15 min), and 0.2 mg/ml of TRITC-phalloidin (20 min).

SEM samples were prepared by bonding the PDMS microfluidic channels onto a polyethylene (PE) film (Diversified Biotech, USA) instead of a glass coverslip. The samples were fixed with 3.7% PFA before the PE film was peeled off to expose the microfluidic channel for SEM processing. Samples were sequentially dehydrated with ethanol series (25, 50, 75, 95 and 100%), and then platinum-sputtered (20 mA, 60 s) before viewing with a field-emission scanning electron microscope (JEOL, Japan).

BMSCs after 1 week of osteogenic induction were stained for calcium salt deposits by von Kossa staining. von Kossa samples were prepared by bonding the PDMS microfluidic channels onto a PE film instead of a glass coverslip, fixed with 3.7% PFA before the PE film was peeled off to expose the microfluidic channel. Effective washing could be achieved to avoid false positive staining. von Kossa staining was carried out with static incubation of the following: 5% silver nitrate solution (45 min), distilled water (DIW) (3×5 min), 5% sodium bicarbonate in 3.7% formaldehyde solution (8 min), DIW (3×5 min), 5% sodium thiosulfate (5 min) and DIW (3×5 min). Likewise, von Kossa staining was performed in 2D monolayer cultures after 1 week of osteogenic induction.

As the BMSC aggregates are withdrawn down the length of the microfluidic channel, they snowballed to form larger cell aggregates, which were then confined by micropillar arrays and accumulated, forming a 3D cellular construct. When a fluorescent label was used to visualize the linkers, fluorescent rings could be seen on cell surfaces, affirming that the cells were aggregated by the linker and supported three-dimensionally by neighboring cells (not shown).

To improve seeding of the 3D cellular aggregates of BMSCs into the compartment of the micro-fluidic channel, improvement of various operational parameters was performed to ensure that the in situ formed cellular aggregates were large enough to be confined by the micropillar arrays and, yet, small enough to prevent clogging of the microfluidic channel. The size of the cellular aggregates can be modulated by the cell density and the inter-cellular linker concentration. A cell density of 5-6 million cells/ml at inter-cellular linker concentration of 6-8 mM was one useful range for effective seeding. At higher cell densities or linker concentrations, massive clogging can occur at the inlet; while at lower cell densities and linker concentrations, ineffective aggregation of cells saw poor cell entrapment. For all subsequent studies, 6 million cells/ml at inter-cellular linker concentration of 6 mM was used. The withdrawal flow rate during cell seeding was improved to be 0.02-0.05 ml/h to ensure high cell viability after the seeding process.

BMSCs were cultured in a system (see FIG. 17B) including the microfluidic continuous flow device 530 which allows the maintenance of a constant cell culture microenvironment over time, without accumulation of metabolites or depletion of oxygen and nutrients that is experienced by re-circulating cultivation cultures. The cultivation medium was oxygenated by passing through oxygen-permeable tubing 570 before entering the bubble trap 550. The perfusion flow rate to culture the 3D cellular construct was 30 µl/h. Other suitable flow rates for cultivation of cells in the compartment have been tested as shown in FIG. 24. Cultivation medium at the end of the perfusion circuit can be collected for assessment of cellular functions.

Cell viability after 3 days of perfusion culture was assessed with fluorescence viability staining and imaged by confocal microscopy. BMSC exhibited good cell viability as can be seen from FIG. 25A.

Actin labeling of the BMSCs showed less stress fibers within the large aggregates (FIG. 25B) than those present in the 2D cultures. Closer examination of the BMSCs using SEM showed that the BMSCs were remodeled into large and tight 3D aggregates with smooth surfaces (FIG. 25C). These results illustrate that BMSCs remained viable and maintained their 3D morphology during the 3-day perfusion culture in the compartment of the microfluidic flow device.

To evaluate the microenvironment for the culture of sensitive primary cells, the differentiation competence of the BMSCs was investigated by differentiating them down the osteogenic lineage. BMSCs in the compartment of the channel were perfused with osteogenic induction medium for 1 week. von Kossa staining for calcium deposits was positive for BMSCs aggregates in the compartment (FIG. 26a), similar to von Kossa staining observed in standard confluent 2D cultures after a 1 week of osteogenic induction (FIG. 26b). This suggests that the microenvironment is useful for the culture and study of sensitive primary cells such as the bone marrow-derived adult stem cells.

Culturing of Primary Rat Hepatocytes in a Microfluidic Continuous Flow Device

FIG. 4 shows the results of the evaluation of albumin secretion from primary rat hepatocytes cultured in a channel of a microfluidic continuous flow device. 200 pg/ml of TGF-β1 was supplemented into cultivation medium (■). In another set of experiment, TGF-β1 was pre-loaded into gelatin microspheres and was then controlled released to the hepatocytes at a concentration of 217.5 pg/ml (▣; control release). In the control experiment, there is no TGF-β1 supplemented in cultivation medium (□).

Albumin production was quantified with a rat albumin ELISA quantification kit (Bethyl Laboratories Inc, USA) in the collected cultivation medium everyday. In the presence of TGF-β1, the level of albumin secretion is enhanced. From day 5 onwards, when TGF-β1 is controlled released to the hepatocytes, the level of albumin secretion can be well-sustained.

FIG. 5 shows the results of the evaluation of 4-MUG production of primary rat hepatocytes cultured in a channel of a microfluidic continuous flow device. 200 pg/ml of TGF-β1 was supplemented into cultivation medium (■). In another set of experiment, TGF-β1 was pre-loaded into gelatin microspheres and was then controlled released to the hepatocytes at a concentration of 217.5 pg/ml (▣). In the control experiment, there is no TGF-β1 supplemented in cultivation medium (□). From day 3 onwards, when TGF-β1 is controlled released to the hepatocytes, the level of 4-MUG production is greatly enhanced.

Similar to the UDP-glucuronosyltransferase (UGT) assay described above, UDP-glucuronosyltransferase (UGT) activity of hepatocytes cultured in the compartment of a channel of a microfluidic continuous flow device was determined by infusing 100 µM of 4-methylumbelliferone (4-MU) (Sigma, Singapore) for 4 h at 200 µl/h into the channel. The perfusate (800 µl) was collected and the metabolic product, 4-methylumbelliferone-glucuronide (4-MUG), was analyzed using capillary electrophoresis with laser induced fluorescence (CE-LIF) (Toh, Y. C. et al., 2008, Analyst, vol. 132, no. 3, p. 326) detection (Prince Technologies B.V., Netherlands) at an excitation wavelength of 325 nm.

What is claimed is:

1. A microfluidic continuous flow device comprising:
a channel comprising (i) a compartment which is defined by partitioning elements and (ii) a space outside said compartment;
wherein through passages which are formed between said partitioning elements are dimensioned to retain a biological material and a sustained release composition within said compartment, wherein the biological material is optionally a cellular biological material and wherein said sustained release composition is adapted to release at least one substance which supports cultivation of said biological material;
wherein said channel has (i') a first inlet to said compartment for introducing said biological material into said compartment, (ii') a second inlet for introducing a cultivation medium into said space of said channel outside of said compartment, and (iii') an outlet;
wherein said second inlet and said outlet are arranged to allow a flow of said cultivation medium through said channel; and
wherein said partitioning elements are pillars; and
wherein a side of said compartment facing said space is defined by the partitioning elements and another side of said compartment is defined by a circumferential wall of said channel.

2. The microfluidic continuous flow device according to claim 1, wherein said channel further comprises a feature selected from the group selected from a medium flow fuser, a medium flow separator, and both a medium flow fuser and a medium flow separator; wherein said medium flow fuser, if present, is located proximal to the channel outlet and; wherein said medium flow separator, if present, is located proximal to the second inlet.

3. A kit comprising the microfluidic continuous flow device according to claim 1, and at least one isolated biological material, wherein the biological material is optionally a cellular biological material, and at least one sustained release composition.

4. A microfluidic continuous flow device comprising:
a first channel and a second channel each comprising (i) a compartment which is defined by partitioning elements and (ii) a space outside the respective first or second compartment;
wherein each of said channels has (i) a first inlet to said compartment, (ii) a second inlet for introducing a cultivation medium into said space of the respective first or second channel outside of said compartment, and (iii) an outlet;
wherein each of said second inlets and each of said outlets are dimensioned and arranged to allow a flow of said cultivation medium through the respective first and/or second channel;

wherein each of said second inlets of said first and second channels is in fluid communication with a common cultivation medium feeding line;

wherein said partitioning elements are pillars having a dimension and arrangement sufficient to retain a biological material in the first and/or second compartment, wherein the biological material is optionally a cellular biological material; and wherein in each channel a side of said compartment facing said space is defined by the partitioning elements and another side thereof is defined by a circumferential wall of said channel.

5. The microfluidic continuous flow device according to claim 4, wherein the pillar dimension and arrangement forms through passages providing fluid communication between the compartment and the space through adjacent partitioning elements.

6. The microfluidic continuous flow device according to claim 4, wherein said first and/or second channels further comprises a feature selected from the group consisting of a medium flow fuser, a medium flow separator, and both a medium flow fuser and a medium flow separator wherein said medium flow fuser, if present, is located proximal to the outlet thereof; and wherein said medium flow separator, if present, is located proximal to the second inlet thereof.

7. A kit comprising the microfluidic continuous flow device according to claim 4, and at least one isolated biological material.

8. A microfluidic continuous flow device comprising:
a first channel and a second channel each comprising (i) a compartment which is defined by partitioning elements and (ii) a space outside the respective first or second compartment;
wherein each of said channels has (i') a first inlet to said compartment, (ii') a second inlet for introducing a cultivation medium into said space of said channel outside of the respective first or second compartment, and (iii') an outlet;
wherein each of said second inlets and each of said outlets are dimensioned and arranged to allow a flow of said cultivation medium through the respective first and/or second channel;
wherein said first and said second channels are fluidly connected to each other, wherein said outlet of said first channel is fluidly connected to said second inlet of said second channel;
wherein said partitioning elements are pillars having a dimension and arrangement sufficient to retain a biological material in the first and/or second compartment, wherein the biological material is optionally a cellular biological material, and
wherein (i") a side of said compartment of said first channel facing said space is defined by the partitioning elements and another side thereof is defined by a circumferential wall of said first channel and/or (ii") a side of said compartment of said second channel facing said space is defined by the partitioning elements and another side thereof is defined by a circumferential wall of said second channel.

9. The microfluidic continuous flow device according to claim 8, wherein the pillar dimension and arrangement forms through passages providing fluid communication between the compartment and the space through adjacent partitioning elements.

10. The microfluidic continuous flow device according to claim 8, wherein said microfluidic continuous flow device further comprises one or more subsequent channels, and wherein said outlet of said first channel is fluidly connected with one or more second inlet of the second and/or the subsequent channels.

11. The microfluidic continuous flow device according to claim 8, wherein said first and/or second channels further comprises a feature selected from the group consisting of a medium flow fuser, a medium flow separator, and both a medium flow fuser and a medium flow separator wherein said medium flow fuser, if present, is located proximal to the outlet thereof; and wherein said medium flow separator, if present, is located proximal to the second inlet thereof.

12. A kit comprising the microfluidic continuous flow device according to claim 3, and at least one isolated biological material.

13. A method of cultivating biological material in a microfluidic continuous flow device, wherein the method comprises:
(a) providing a microfluidic continuous flow device comprising:
a channel comprising (i) a compartment which is defined by partitioning elements and (ii) a space outside said compartment;
wherein through passages which are formed between said partitioning elements are dimensioned and arranged to retain a biological material and a sustained release composition within said compartment, wherein the biological material is optionally a cellular biological material and wherein the sustained release composition is adapted to release at least one substance which supports cultivation of said biological material;
wherein said channel has (i') a first inlet to said compartment for introducing said biological material into said compartment, (ii') a second inlet for introducing a cultivation medium into said space of said channel outside of said compartment, and (iii') an outlet;
wherein said second inlet and said outlet are arranged to allow a flow of said cultivation medium through said channel;
wherein said partitioning elements are pillars; and
wherein a side of said compartment facing said space is defined by the partitioning elements and another side of said compartment is defined by a circumferential wall of said channel;
(b) introducing a biological material and a sustained release composition into the compartment via the first inlet, wherein said sustained release composition releases at least one substance which supports cultivation of the biological material and which said at least one released substance is not present in said cultivation medium prior to the introducing; and
(c) transporting the cultivation medium from the second inlet through said channel in sufficient amount to culture said biological material, thereby cultivating the biological material.

14. The method according to claim 13, further comprising introducing polyelectrolytes together with said biological material into said compartment or introducing said polyelectrolytes into said compartment before introducing said biological material into said compartment.

15. The method according to claim 13, further comprising introducing a test substance into said cultivation medium.

16. The method according to claim 13, further comprising transporting a second medium comprising a test substance through said channel.

17. A method of cultivating biological material in a microfluidic continuous flow device, wherein the method comprises:
(a) providing a microfluidic continuous flow device comprising:
a first channel and a second channel each comprising (i) a compartment which is defined by partitioning elements and (ii) a space outside the respective first and second compartments;
wherein each of said channels has (i) a first inlet to said compartment, (ii') a second inlet for introducing a cultivation medium into said space of the respective first or second channel outside of said compartment, and (iii') an outlet;
wherein each of said second inlets and each of said outlets are dimensioned and arranged to allow a flow of said cultivation medium through the respective first and/or second channel;
wherein each of said second inlets of said first and second channels is in fluid communication with a common cultivation medium feeding line;
wherein said partitioning elements are pillars having a dimension and arrangement sufficient to retain a biological material in the first and/or second compartment, wherein the biological material is optionally a cellular biological material; and
wherein in each channel a side of said compartment facing said space is defined by the partitioning elements and another side thereof is defined by a circumferential wall of said channel;
(b) introducing a biological material into each of said compartments via each of said respective first inlets;
(c) transporting the cultivation medium from said common cultivation medium feeding line through each of said first and second channels in an amount sufficient to culture said biological material, thereby cultivating the biological material.

18. The method according to claim 17, further comprising introducing polyelectrolytes together with said biological material into said compartment or compartments or introducing said polyelectrolytes into said compartment or compartments before introducing said biological material into said compartment or compartments.

19. The method according to claim 17, further comprising introducing a test substance into said cultivation medium.

20. The method according to claim 17, further comprising transporting a second medium comprising a test substance through each of said channels.

21. A method of cultivating biological material in a microfluidic continuous flow device, wherein the method comprises:
(a) providing a microfluidic continuous flow device comprising:
a first channel and a second channel each comprising (i) a compartment which is defined by partitioning elements and (ii) a space outside the respective first or second compartment;
wherein each of said channels has (i') a first inlet to said compartment, (ii') a second inlet for introducing a cultivation medium into said space of said channel outside of the respective first or second compartment, and (iii') an outlet;
wherein each of said second inlets and each of said outlets are dimensioned and arranged to allow a flow of said cultivation medium through the respective first and/or second channel;
wherein said first and said second channels are fluidly connected to each other, wherein said outlet of said first channel is fluidly connected to said second inlet of said second channel; wherein said partitioning elements are pillars having a dimension and arrangement sufficient to retain a biological material in the first and/or second compartment, wherein the biological material is optionally a cellular biological material, and
wherein (i") a side of said compartment of said first channel facing said space is defined by the partitioning elements and another side thereof is defined by a circumferential wall of said first channel and/or (ii") a side of said compartment of said second channel facing said space is defined by the partitioning elements and another side thereof is defined by a circumferential wall of said second channel;
(b) introducing a biological material into each of said compartments via each of said respective first inlets;
(c) transporting the cultivation medium from said second inlets of said first and second channels through said first and second channels respectively, in amounts sufficient to culture said biological material, thereby cultivating the biological material.

22. The method according to claim 21, further comprising introducing polyelectrolytes together with said biological material into said compartment or compartments or introducing said polyelectrolytes into said compartments before introducing said biological material into said compartment or compartments.

23. The method according to claim 21, further comprising introducing a test substance into said cultivation medium.

24. The method according to claim 21, further comprising transporting a second medium comprising a test substance through each of said channels.

* * * * *